US011246835B2

(12) United States Patent
Baniel et al.

(10) Patent No.: US 11,246,835 B2
(45) Date of Patent: Feb. 15, 2022

(54) METHOD FOR PRODUCING SWEETENER COMPOSITIONS AND SWEETENER COMPOSITIONS

(71) Applicant: DOUXMATOK LTD, Tel-Aviv (IL)

(72) Inventors: Avraham Baniel, Jerusalem (IL); Michael Zviely, Haifa (IL); Shay Eliyahu, Tel-Aviv (IL); Noa Gelbart, Herzliya (IL); Eran Baniel, Tel-Aviv (IL); Ronit Romm, Jerusalem (IL)

(73) Assignee: DOUXMATOK LTD, Tel Aviv (IL)

( * ) Notice: Subject to any disclaimer, the term of this patent is extended or adjusted under 35 U.S.C. 154(b) by 0 days.

(21) Appl. No.: 16/882,346

(22) Filed: May 22, 2020

(65) Prior Publication Data

US 2020/0383920 A1    Dec. 10, 2020

Related U.S. Application Data

(63) Continuation of application No. 15/045,145, filed on Feb. 16, 2016, now abandoned, which is a continuation of application No. PCT/IB2015/000773, filed on Apr. 3, 2015, which is a continuation-in-part of application No. 14/629,272, filed on Feb. 23, 2015, now Pat. No. 10,207,004.

(60) Provisional application No. 62/074,518, filed on Nov. 3, 2014, provisional application No. 62/042,154, filed on Aug. 26, 2014, provisional application No. 61/975,683, filed on Apr. 4, 2014.

(51) Int. Cl.
| | |
|---|---|
| *A61K 9/16* | (2006.01) |
| *A23L 27/30* | (2016.01) |
| *A23L 2/60* | (2006.01) |
| *A23L 29/30* | (2016.01) |
| *A23L 27/00* | (2016.01) |
| *A23G 3/42* | (2006.01) |
| *A23G 1/40* | (2006.01) |
| *A23G 9/34* | (2006.01) |
| *A61K 47/36* | (2006.01) |

(52) U.S. Cl.
CPC ............ *A61K 9/1611* (2013.01); *A23G 1/40* (2013.01); *A23G 3/42* (2013.01); *A23G 9/34* (2013.01); *A23L 2/60* (2013.01); *A23L 27/30* (2016.08); *A23L 27/32* (2016.08); *A23L 27/33* (2016.08); *A23L 27/34* (2016.08); *A23L 27/70* (2016.08); *A23L 27/84* (2016.08); *A23L 29/30* (2016.08); *A23L 29/35* (2016.08); *A23L 29/37* (2016.08); *A61K 9/1652* (2013.01); *A23V 2002/00* (2013.01); *A61K 9/1623* (2013.01); *A61K 47/36* (2013.01)

(58) Field of Classification Search
CPC .. A61K 9/1611; A61K 9/1623; A61K 9/1652; A61K 47/36; A23L 29/35; A23L 2/60; A23G 1/40; A23G 3/42; A23G 9/34

USPC ........................................................ 426/499
See application file for complete search history.

(56) References Cited

U.S. PATENT DOCUMENTS

| | | |
|---|---|---|
| 3,175,299 A | 3/1965 | Boucher |
| 3,503,803 A | 3/1970 | Richard et al. |
| 3,655,578 A | 4/1972 | Paul |
| 3,704,138 A | 11/1972 | Via et al. |
| 3,988,162 A | 10/1976 | Wason |
| 4,016,337 A | 4/1977 | Hsu |
| 4,021,582 A | 5/1977 | Hsu |
| 4,343,820 A | 8/1982 | Roseman |
| 4,513,012 A | 4/1985 | Carroll et al. |
| 4,626,287 A | 12/1986 | Shah et al. |
| 4,659,388 A | 4/1987 | Innami et al. |
| 4,671,823 A | 6/1987 | Shah et al. |
| 4,752,485 A | 6/1988 | Sharma et al. |
| 4,774,099 A | 9/1988 | Feeney et al. |
| 4,925,693 A | 5/1990 | Lauly |
| 4,976,972 A | 12/1990 | Patel et al. |
| 4,981,698 A | 1/1991 | Cherukuri et al. |
| 5,133,977 A | 7/1992 | Patel |
| 5,145,707 A | 9/1992 | Lee |
| 5,252,136 A | 10/1993 | Desforges et al. |
| 5,260,091 A | 11/1993 | Locke et al. |
| 5,266,335 A | 11/1993 | Cherukuri et al. |
| 5,314,810 A | 5/1994 | Kono et al. |
| 5,338,809 A | 8/1994 | Bell et al. |
| 5,411,730 A | 5/1995 | Kirpotin et al. |
| 5,492,814 A | 2/1996 | Weissleder |
| 5,603,920 A | 2/1997 | Rice |
| 5,651,958 A | 7/1997 | Rice |
| 5,709,896 A | 1/1998 | Hartigan et al. |
| 5,711,985 A | 1/1998 | Guerrero et al. |
| 5,912,030 A | 6/1999 | Huzinec et al. |
| 6,123,926 A | 9/2000 | Parikh et al. |
| 6,248,378 B1 | 6/2001 | Gañán-Calvo |
| 6,251,464 B1 | 6/2001 | Felisaz et al. |

(Continued)

FOREIGN PATENT DOCUMENTS

| | | |
|---|---|---|
| AU | 2012202679 B2 | 3/2014 |
| CN | 2072973 U | 3/1991 |

(Continued)

OTHER PUBLICATIONS

U.S. Appl. No. 15/576,681 Office Action dated Jul. 22, 2020.

(Continued)

*Primary Examiner* — Jyoti Chawla

(74) *Attorney, Agent, or Firm* — Wilson Sonsini Goodrich & Rosati

(57) ABSTRACT

Provided herein are compositions with enhanced sweetness or reduced caloric content per weight when compared to the sweetener carbohydrate or sweetener polyol component thereof, and methods for the preparation thereof.

20 Claims, 5 Drawing Sheets

(56) References Cited

U.S. PATENT DOCUMENTS

| | | |
|---|---|---|
| 6,428,827 B1 | 8/2002 | Song et al. |
| 6,461,658 B1 | 10/2002 | Merkel et al. |
| 6,548,264 B1 | 4/2003 | Tan et al. |
| 6,652,611 B1 | 11/2003 | Huang et al. |
| 6,673,383 B2 | 1/2004 | Cain et al. |
| 6,703,057 B2 | 3/2004 | Duffett |
| 6,777,397 B2 | 8/2004 | Zehner et al. |
| 7,118,765 B2 | 10/2006 | Norman et al. |
| 7,122,215 B2 | 10/2006 | Ludwig et al. |
| 7,163,708 B2 | 1/2007 | Dalziel et al. |
| 7,258,885 B2 | 8/2007 | Seltzer et al. |
| 7,267,835 B2 | 9/2007 | Kitazume et al. |
| 7,282,217 B1 | 10/2007 | Grimshaw et al. |
| 7,544,379 B2 | 6/2009 | Kawamura et al. |
| 7,744,922 B2 | 6/2010 | Mane et al. |
| 7,754,239 B2 | 7/2010 | Mane et al. |
| 7,763,570 B1 | 7/2010 | Rayborn, Sr. et al. |
| 7,815,936 B2 | 10/2010 | Hasenzahl et al. |
| 7,838,033 B2 | 11/2010 | Tanaka et al. |
| 7,838,055 B2 | 11/2010 | Eroma et al. |
| 7,842,324 B2 | 11/2010 | Tachdjian et al. |
| 7,851,005 B2 | 12/2010 | Hargreaves et al. |
| 7,851,006 B2 | 12/2010 | Bingley et al. |
| 7,879,376 B2 | 2/2011 | Boghani et al. |
| 7,955,630 B2 | 6/2011 | Boghani et al. |
| 7,972,995 B2 | 7/2011 | Rayborn, Sr. et al. |
| 8,119,173 B2 | 2/2012 | Cheng et al. |
| 8,192,775 B2 | 6/2012 | Eroma et al. |
| 8,216,981 B2 | 7/2012 | Rayborn, Sr. et al. |
| 8,349,361 B2 | 1/2013 | Tanaka et al. |
| 8,545,889 B2 | 10/2013 | Norman et al. |
| 8,617,588 B2 | 12/2013 | Tillotson et al. |
| 8,647,668 B2 | 2/2014 | Tanaka et al. |
| 8,663,682 B2 | 3/2014 | Chenevier et al. |
| 8,673,825 B2 | 3/2014 | Rayborn, Sr. et al. |
| 8,697,167 B2 | 4/2014 | Stouffs et al. |
| 8,911,806 B2 | 12/2014 | Baniel |
| 8,962,058 B2 | 2/2015 | Prakash et al. |
| 9,023,418 B2 | 5/2015 | Baniel |
| 9,028,906 B2 | 5/2015 | Baniel |
| 9,144,251 B2 | 9/2015 | Prakash et al. |
| 9,271,942 B2 | 3/2016 | Ramtoola |
| 9,358,212 B2 | 6/2016 | Tillotson et al. |
| 9,446,055 B2 | 9/2016 | Fujiwara et al. |
| 9,668,504 B2 | 6/2017 | Baniel et al. |
| 10,207,004 B2 | 2/2019 | Baniel et al. |
| 10,212,961 B2 | 2/2019 | Baniel et al. |
| 10,231,476 B2 | 3/2019 | Baniel et al. |
| 10,244,782 B2 | 4/2019 | Baniel et al. |
| 2001/0004869 A1 | 6/2001 | Cantiani et al. |
| 2001/0055572 A1 | 12/2001 | Thomas et al. |
| 2003/0014014 A1 | 1/2003 | Nitzan |
| 2003/0039617 A1 | 2/2003 | White et al. |
| 2003/0129227 A1 | 7/2003 | Yamaguchi |
| 2004/0161498 A1 | 8/2004 | Ripoll et al. |
| 2005/0130240 A1 | 6/2005 | Lin et al. |
| 2005/0244568 A1 | 11/2005 | Gokhan |
| 2006/0024335 A1 | 2/2006 | Roger |
| 2006/0051480 A1 | 3/2006 | Miles |
| 2006/0073255 A1 | 4/2006 | Catani et al. |
| 2007/0003680 A1 | 1/2007 | Tachdjian et al. |
| 2007/0092562 A1 | 4/2007 | Norman et al. |
| 2007/0116827 A1 | 5/2007 | Prakash et al. |
| 2007/0116828 A1 | 5/2007 | Prakash et al. |
| 2007/0116832 A1 | 5/2007 | Prakash et al. |
| 2008/0044521 A1 | 2/2008 | Eddies et al. |
| 2008/0102163 A1 | 5/2008 | O'Toole et al. |
| 2008/0193531 A1 | 8/2008 | Hermelin et al. |
| 2008/0213452 A1 | 9/2008 | Miles et al. |
| 2008/0292765 A1 | 11/2008 | Prakash et al. |
| 2008/0311398 A1 | 12/2008 | Bauer et al. |
| 2009/0053378 A1 | 2/2009 | Prakash et al. |
| 2009/0220664 A1 | 9/2009 | Tate et al. |
| 2010/0129516 A1 | 5/2010 | Siegel |
| 2011/0027355 A1 | 2/2011 | Lefevre et al. |
| 2011/0027444 A1 | 2/2011 | Gelov |
| 2011/0052755 A1 | 3/2011 | Fiorenza et al. |
| 2011/0059218 A1 | 3/2011 | Corliss et al. |
| 2011/0064861 A1 | 3/2011 | Shimono et al. |
| 2011/0195170 A1 | 8/2011 | Shigemura et al. |
| 2012/0207890 A1 | 8/2012 | Johal et al. |
| 2013/0236604 A1 | 9/2013 | De Baets |
| 2013/0273165 A1 | 10/2013 | Buchner |
| 2013/0283165 A1 | 10/2013 | Hua |
| 2014/0010939 A1 | 1/2014 | Krohn et al. |
| 2014/0044858 A1 | 2/2014 | Quevedo |
| 2014/0271747 A1 | 9/2014 | Woodyer et al. |
| 2015/0018432 A1 | 1/2015 | Prakash et al. |
| 2015/0150292 A1 | 6/2015 | Baniel |
| 2015/0189904 A1 | 7/2015 | Prakash et al. |
| 2015/0275319 A1 | 10/2015 | Baniel |
| 2015/0289550 A1 | 10/2015 | Baniel et al. |
| 2016/0045518 A1 | 2/2016 | Dohil et al. |
| 2016/0242439 A1 | 8/2016 | Baniel et al. |
| 2018/0249744 A1 | 9/2018 | Baniel et al. |
| 2019/0000123 A1 | 1/2019 | Baniel et al. |
| 2019/0021381 A1 | 1/2019 | Baniel |
| 2019/0150492 A1 | 5/2019 | Baniel |
| 2019/0289889 A1 | 9/2019 | Baniel et al. |

FOREIGN PATENT DOCUMENTS

| | | |
|---|---|---|
| CN | 101049150 A | 10/2007 |
| CN | 100408016 C | 8/2008 |
| CN | 103504256 A | 1/2014 |
| CN | 103584062 A | 2/2014 |
| CN | 103864899 A | 6/2014 |
| EP | 0350419 A2 | 1/1990 |
| EP | 0427541 A2 | 5/1991 |
| EP | 1447074 A2 | 8/2004 |
| EP | 1817964 A1 | 8/2007 |
| EP | 1901617 A1 | 3/2008 |
| EP | 1901617 B1 | 10/2009 |
| FR | 2808657 B1 | 6/2003 |
| GB | 721605 A | 1/1955 |
| GB | 2025227 A | 1/1980 |
| HK | 1158629 A1 | 10/2015 |
| IL | 169678 A | 11/2010 |
| IL | 180687 A | 4/2011 |
| JP | H04364122 A | 12/1992 |
| JP | 2001352936 A | 12/2001 |
| NZ | 556774 A | 2/2011 |
| WO | WO-9012117 A2 | 10/1990 |
| WO | WO-9414330 A1 | 7/1994 |
| WO | WO-9416576 A1 | 8/1994 |
| WO | WO-9526645 A1 | 10/1995 |
| WO | WO-9920127 A1 | 4/1999 |
| WO | WO-0113740 A1 | 3/2001 |
| WO | WO-02051391 A2 | 7/2002 |
| WO | WO-02096213 A1 | 12/2002 |
| WO | WO-03045166 A1 | 6/2003 |
| WO | WO-2004005227 A1 | 1/2004 |
| WO | WO-2004066974 A1 | 8/2004 |
| WO | WO-2004089113 A1 | 10/2004 |
| WO | WO-2004098555 A1 | 11/2004 |
| WO | WO-2005037254 A1 | 4/2005 |
| WO | WO-2005037849 A1 | 4/2005 |
| WO | WO-2005084457 A1 | 9/2005 |
| WO | WO-2006012763 A1 | 2/2006 |
| WO | WO-2006015880 A1 | 2/2006 |
| WO | WO-2006062089 A1 | 6/2006 |
| WO | WO-2006072921 A2 | 7/2006 |
| WO | WO-2007007310 A1 | 1/2007 |
| WO | WO-2007061757 A1 | 5/2007 |
| WO | WO-2007061810 A2 | 5/2007 |
| WO | WO-2007061858 A1 | 5/2007 |
| WO | WO-2007061900 A1 | 5/2007 |
| WO | WO-2007061912 A2 | 5/2007 |
| WO | WO-2007081442 A2 | 7/2007 |
| WO | WO-2008010405 A1 | 1/2008 |
| WO | WO-2008042417 A1 | 4/2008 |
| WO | WO-2009006208 A2 | 1/2009 |
| WO | WO-2009087215 A2 | 7/2009 |
| WO | WO-2009151072 A1 | 12/2009 |

(56) References Cited

FOREIGN PATENT DOCUMENTS

| | | |
|---|---|---|
| WO | WO-2010025158 A1 | 3/2010 |
| WO | WO-2011019045 A1 | 2/2011 |
| WO | WO-2012171086 A1 | 12/2012 |
| WO | WO-2013045318 A1 | 4/2013 |
| WO | WO-2013082019 A1 | 6/2013 |
| WO | WO-2014080394 A1 | 5/2014 |
| WO | WO-2015015210 A1 | 2/2015 |
| WO | WO-2015041984 A1 | 3/2015 |
| WO | WO-2015150915 A2 | 10/2015 |
| WO | WO-2015159156 A2 | 10/2015 |
| WO | WO-2015159156 A3 | 2/2016 |
| WO | WO-2015150915 A3 | 3/2016 |
| WO | WO-2016189385 A2 | 12/2016 |
| WO | WO-2017037531 A2 | 3/2017 |
| WO | WO-2017037531 A3 | 4/2017 |

OTHER PUBLICATIONS

U.S. Appl. No. 15/756,040 Office Action dated Oct. 1, 2020.
U.S. Appl. No. 15/756,042 Office Action dated Nov. 12, 2020.
U.S. Appl. No. 16/252,328 Office Action dated Aug. 24, 2020.
Al-Ghouti, et al. New adsorbents based on microemulsion modified diatomite and activated carbon for removing organic and inorganic pollutants from waste lubricants. Chemical Engineering Journal vol. 173, Issue Sep. 1, 2011, 115-128.
Bergna, Horacio E, Ed. The Colloidal Chemistry of Silica, ACS Publications, p. 21-30, 341-353, 1994.
DOWEX Ion Exchange Resins. Jun. 2002. 12 pages.
EP16840895.3 Extended European Search Report dated Jan. 18, 2019.
EP16859143.6 Extended European Search Report dated Jan. 25, 2019.
European search report and search opinion dated Oct. 27, 2017 for European Patent Application No. 15780074.9.
Grandinetti Laboratory (undated). Retrieved Jun. 27, 2019 at URL: https://www.grandinetti.org/vsepr.
Hafiz, et al. Synthesis of quality silica gel; Optimization of parameters. Journal of Faculty of Engineering & Technology, 2009, 14 pages.
Handbuch Subungsmittel: Eigenschaften and Anwendung. pp. 162-165. G.W. von Rymon Lipinski and H. Hamburg, Germany (1990). ISBN: 3-925673-77-6 (in German).
International search report and written opinion dated Jan. 7, 2016 for PCT Application No. PCT-IB15-00773.
International Search Report and Written Opinion dated Feb. 9, 2017 for PCT Application No. PCT/IB2016/01322.
International Search Report and Written Opinion dated Feb. 16, 2017 for PCT Application No. PCT/IB2016/01284.
International search report and written opinion dated Apr. 4, 2014 for PCT Application No. IL2013/050851.
International search report and written opinion dated Jul. 20, 2006 for PCT Application No. IL2006/00573.
"International search report and written opinion dated Nov. 30, 2015 for PCT/IB2015/001153.".
"International search report with written opinion dated Dec. 12, 2016 for PCT/IB2016/00818".
Kelly, et al. Phase Equilibria in the System Sucrose-Glucose-Fructose. J. appl. Chem. May 4, 1967. 17.5: 125-126.
Kinrade, et al. Aqueous hypervalent silicon complexes with aliphatic sugar acids. J. Chem. Soc., Dalton Trans., 2001 ,0, 961-963.
Kinrade, et al. Silicon-29 NMR evidence of alkoxy substituted aqueous silicate anions. J. Chem. Soc., Dalton Trans., 1999, 3149-3150.
Kinrade, et al. Stable five- and six-coordinated silicate anions in aqueous solution. Science. Sep. 3, 1999;285(5433):1542-5.
Lionnet, et al. Aspects of the Effects of Silica During Cane Sugar Processing. Proc S Afr Sug Technol Ass. vol. 78. 2004, 55-64.
Madho, et al. Silica in low grade refinery sugar Proc S Afr Sug Technol Ass. vol. 84. 2011, 516-527.

Martin, K.R. The Chemistry of Silica and its Potential Health Benefits. The Journal of Nutrition, Health & Aging; Paris vol. 11(2), (Mar./Apr. 2007): 94-7.
Middle School Chemistry (copyright 2012) http://www.middleschoolchemistry.com/multimedia/chapter4/lesson6.
Narducci, Olga. Particle Engineering via Sonocrystallization: The Aqueous Adipic Acid System. University College of London: Department of Chemical Engineering. p. 65 of Ph.D. Thesis. Oct. 2012. 2 pages.
Notice of Allowance dated Jan. 2, 2015 for U.S. Appl. No. 13/250,088.
Notice of allowance dated Feb. 13, 2015 for U.S. Appl. No. 14/511,046.
Notice of allowance dated Mar. 22, 2017 for U.S. Appl. No. 14/528,750.
Notice of allowance dated Oct. 6, 2014 for U.S. Appl. No. 11/995,464.
Office action dated Jan. 7, 2013 for U.S. Appl. No. 13/250,088.
Office action dated Jan. 10, 2013 for U.S. Appl. No. 11/995,464.
Office action dated Jan. 10, 2014 for U.S. Appl. No. 11/995,464.
Office action dated Jan. 22, 2016 for U.S. Appl. No. 14/629,272.
Office action dated Mar. 28, 2016 for U.S. Appl. No. 14/440,975.
Office action dated Apr. 18, 2012 for U.S. Appl. No. 11/995,464.
Office action dated Apr. 27, 2017 for U.S. Appl. No. 15/222,916.
Office action dated May 30, 2013 for U.S. Appl. No. 13/250,088.
Office action dated Jul. 30, 2014 for U.S. Appl. No. 13/250,088.
Office action dated Aug. 15, 2011 for U.S. Appl. No. 11/995,464.
Office action dated Sep. 10, 2014 for U.S. Appl. No. 13/250,088.
Office action dated Sep. 18, 2017 for U.S. Appl. No. 15/487,274.
Office action dated Oct. 6, 2017 for U.S. Appl. No. 15/222,916.
Office action dated Nov. 18, 2016 for U.S. Appl. No. 14/528,750.
Office action dated Dec. 29, 2016 for U.S. Appl. No. 14/629,272.
Pending claims dated May 15, 2014 for U.S. Appl. No. 13/250,088.
Pending claims dated Aug. 28, 2014 for U.S. Appl. No. 13/250,088.
Rombauer, I. S., Rombauer Becker, M., Becker, E. 1997. Joy of Cooking. Scribner: New York. p. 1010.
Smith, Jim; Hong-Shum, Lily (2003). Food Additives Data Book, (pp. 704-707). Blackwell Publishing. Online version available at: http://www.knovel.com/web/portal/browse/display?_EXT_KNOVEL_DISPLAY_bookid=1381&VerticalID=.
Storer, Ian. Hypervalent Silicon: Bonding, Properties and Synthetic Utility, MacMillan Group Meeting, Jul. 20, 2005.
"Tamura M, et al. An enhancing effect on the saltiness of sodium chloride of added amino acids and their esters. Agricultural and Biological Chemistry. 1989, vol. 53, No. 6, pp. 1625-1633".
U.S. Appl. No. 14/629,272 Notice of Allowance dated Jan. 3, 2019.
U.S. Appl. No. 14/629,272 Notice of Allowance dated Sep. 25, 2018.
U.S. Appl. No. 14/629,272 Office Action dated Jun. 18, 2018.
U.S. Appl. No. 15/487,274 Notice of Allowance dated Nov. 9, 2018.
U.S. Appl. No. 15/487,274 Office Action dated Aug. 16, 2018.
U.S. Appl. No. 15/489,696 Notice of Allowance dated Jan. 2, 2019.
U.S. Appl. No. 15/756,040 Office Action dated Oct. 2, 2019.
U.S. Appl. No. 14/629,272 Notice of Allowance dated Oct. 17, 2018.
U.S. Appl. No. 14/629,272 Notice of Allowance dated Oct. 5, 2018.
U.S. Appl. No. 15/222,916 Office Action dated Feb. 28, 2018.
U.S. Appl. No. 15/487,274 Office Action dated Feb. 9, 2018.
U.S. Appl. No. 15/489,696 Office Action dated Mar. 13, 2018.
U.S. Appl. No. 15/222,916 Notice of Allowance dated Jan. 9, 2019.
U.S. Appl. No. 15/222,916 Notice of Allowance dated Oct. 25, 2018.
U.S. Appl. No. 15/489,696 Notice of Allowance dated Dec. 12, 2018.
U.S. Appl. No. 15/489,696 Notice of Allowance dated Oct. 4, 2018.
Zhuravlev, L.T. The surface chemistry of amorphous silica. Zhuravlev model. Colliods and Surfaces. A:Physicochemical and Engineering Aspects, 173:1-38, 2000.
Co-pending U.S. Appl. No. 14/677,715, filed Apr. 2, 2015.
Godshall. Chapter 10: Role of sucrose in retention of aroma and enhancing the flavor of foods, Sucrose Properties and Applications, pp. 248-263. Springer Science+Business Media Dordrecht, First Edition (1995).
Office action dated May 9, 2016 for U.S. Appl. No. 14/528,750.
Office action dated May 25, 2016 for U.S. Appl. No. 14/629,272.
Office action dated Aug. 15, 2016 for U.S. Appl. No. 15/045,145.

(56) References Cited

OTHER PUBLICATIONS

Poste et al, Laboratory Methods for Sensory Analysis of Food, Research Branch Agriculture Canada Publication 1864/E, p. 1 (1991). Retrieved Apr. 8, 2020 from URL: https://archive.org/details/laboratorymethod00otta/mode/2up.
Reiser et al. Chapter 8: Physical Properties, Sucrose Properties and Applications, pp. 186-222. Springer Science+Business Media Dordrecht, First Edition (1995).
U.S. Appl. No. 15/045,145 Office Action dated Aug. 9, 2019.
U.S. Appl. No. 15/045,145 Office Action dated Mar. 12, 2019.
U.S. Appl. No. 16/252,328 Office Action dated Jan. 10, 2020.
U.S. Appl. No. 15/045,145 Office Action dated Feb. 26, 2020.
U.S. Appl. No. 15/756,040 Office Action dated Apr. 2, 2020.
U.S. Appl. No. 15/576,681 Office Action dated Jun. 24, 2021.
U.S. Appl. No. 15/756,040 Office Action dated Jun. 15, 2021.
U.S. Appl. No. 15/576,681 Office Action dated Dec. 24, 2020.
U.S. Appl. No. 16/252,328 Office Action dated Mar. 4, 2021.
U.S. Appl. No. 16/275,213 Office Action dated Feb. 16, 2021.

METHOD FOR PRODUCING SWEETENER COMPOSITIONS AND SWEETENER COMPOSITIONS

CROSS-REFERENCE

This application is a continuation application of U.S. application Ser. No. 15/045,145, filed on Feb. 16, 2016, which is a continuation of International Application No. PCT/IB2015/000773, filed on Apr. 3, 2015, which is a continuation-in-part of U.S. application Ser. No. 14/629,272, filed Feb. 23, 2015, now U.S. Pat. No. 10,207,004, which application claims priority from U.S. Provisional Application No. 62/074,518, filed Nov. 3, 2014, U.S. Provisional Application No. 62/042,154, filed Aug. 26, 2014, U.S. Provisional Application No. 61/975,683, filed Apr. 4, 2014 all of which are incorporated herein by reference in their entirety.

FIELD OF THE INVENTION

The present disclosure relates to sweetener compositions. More particularly, the present invention relates to carbohydrate sweetener compositions and polyol sweetener compositions having enhanced sweetness and reduced caloric content as compared to that of the carbohydrate component or polyol component thereof, and to methods for the preparation thereof.

BACKGROUND OF THE INVENTION

Certain carbohydrates and polyols are commonly used as sweeteners. Sucrose, glucose, and other sweet mono-saccharides, di-saccharides, and oligosaccharides are fully metabolized when consumed in food. The sweetness of these natural sweeteners correlates with their calories in a fixed proportion. Excess sugar intake can pose several health problems. Artificial sweeteners have been used to reduce dietary sugar content, but they are not ideal sugar substitutes due to their after taste, absence of energy provided by sugars, and other health concerns. Sweetener polyols can offer a reduced calorie load and varying sweetness as compared to sweetener carbohydrates, but the cost of some sweetener polyols can be high. In such cases, a method to increase the sweetness of sweetener carbohydrates or sweetener polyols or to reduce the amount of sweetener carbohydrates or sweetener polyols while achieving equivalent sweetness is desired. Another promising strategy focuses on allosteric modulation of the sweet taste receptor by sweet taste enhancers. These artificially synthesized molecules do not taste sweet but can significantly modulate the perception of sweetness for sucrose and other sweeteners; however, they can be limited in strength and selectivity and have so far been tested on limited products. The present disclosure provides for the manipulation of the proportion between sweetener amount and calories so that a desired sweetness may correlate with lower calorie values while retaining a similar sensory profile to the sweetener. This effect is achieved through the presentation of the carbohydrate sweetener or polyol sweetener in the form of a composition belonging to a class of compositions described below. The perception of sweetness of a sweetener carbohydrate or sweetener polyol is retained while reducing the caloric value thereof by virtue of it being provided in a composition as described hereinafter.

SUMMARY OF THE INVENTION

Provided herein is a method of making a sweetener composition, comprising mechanically coating a carrier compound with one or more sweetener carbohydrates or sweetener polyols; wherein the sweetener composition has enhanced sweetness compared to a control composition; and wherein the control composition consists of the same contents by identity and quantity as the sweetener composition but without the carrier compound. In some embodiments, the method comprises sonicating the sweetener composition to form a sonicated sweetener composition. In some embodiments, the method comprises passing the sweetener composition through a sieve or sieving tower to remove particles of particular sizes and to form a selectively sieved sweetener composition. In some embodiments, the mechanical coating is by mortar and pestle or mechanical grinder. In some embodiments, the sweetness is enhanced by at least 10, 20, 30, 40 or 50%, for example, the sweetness is enhanced by 40-60%.

Further provided herein is a sweetener composition comprising one or more sweetener carbohydrates and/or sweetener polyols and 6-12% carrier compound weight/weight (wt/wt) relative to a sum of total sweetener carbohydrate and sweetener polyol; wherein the sweetener composition has enhanced sweetness compared to a control composition; and wherein the control composition consists of the same contents by identity and quantity as the sweetener composition but without the carrier compound. In some embodiments, the compositions comprises about 8-10% carrier compound wt/wt relative to a sum of total sweetener carbohydrate and sweetener polyol, for example, 8% carrier compound wt/wt relative to a sum of total sweetener carbohydrate and sweetener polyol. In some embodiments, the one or more sweetener carbohydrates are high fructose corn syrup. In some embodiments, the one or more sweetener carbohydrates are high maltose corn syrup. In some embodiments, each of the one or more sweetener carbohydrates is selected from the group consisting of sucrose and glucose. In some embodiments, the one or more sweetener carbohydrates are sucrose, glucose, maltose, lactose, high fructose corn syrup, high maltose corn syrup, or a combination thereof. In some embodiments, the one or more sweetener carbohydrates are not fructose. In some embodiments, the composition comprises a sweetener polyol. In some embodiments, the sweetener polyol is selected from the group consisting of xylitol, maltitol, erythritol, and sorbitol. In some embodiments, the sweetener polyol is xylitol, maltitol, erythritol, sorbitol, threitol, arabitol, hydrogenated starch hydrolysates (HSH), isomalt, lactitol, mannitol, galactitol (dulcitol), and a combination thereof. In some embodiments, the composition comprises one or more sweetener carbohydrates, one or more sweetener polyols, or a combination thereof. In some cases, the sweetener composition is an isolated sweetener composition. In some cases, a sweetener composition described herein reduces the perceived bitterness of a consumable product, such as a food, beverage, or other non-food, non-beverage consumable product.

In some embodiments, the carrier compound is chitosan. In some embodiments, the carrier compound is silica. In some embodiments, the carrier compound is precipitated silica. In some embodiments, the carrier compound is porous silica. In some embodiments, the carrier compound is porous, precipitated silica. In some embodiments, the carrier compound is silica gel. In some embodiments, the carrier compound is amorphous silica. In some embodiments, the carrier compound is precipitated, amorphous silica. In some embodiments, the carrier compound is Perkasil® (W. R. Grace & Co). In some embodiments, the carrier compound is Perkasil® SM 660 (W. R. Grace & Co). In some embodiments, the carrier compound is SYLOID® (W. R. Grace &

Co). In some embodiments, the carrier compound is SYLOX® (W. R. Grace & Co). In some embodiments, the carrier compound is Tixosil® (Solvay). In some embodiments, the carrier compound is Tixosil® 38AB (Solvay). In some embodiments, the carrier compound contains a moisture level or water content of 0 to 6% by weight (wt).

In some embodiments, a sweetener composition is formulated as particles. In some embodiments, at least 50 percent of the particles of the sweetener composition are between about 25 microns and about 200 microns in diameter. In some embodiments, at least 50 percent of the particles of the sweetener composition are between about 25 microns and about 74 microns in diameter.

In some embodiments, the composition is comprised of at least 10%, 20%, 30%, 40%, 50%, 60%, 70%, 80%, 90%, or 95% sweetener carbohydrate and carrier compound by weight. In some embodiments, the composition consists essentially of sweetener carbohydrate and carrier compound. In some embodiments, the composition consists of sweetener carbohydrate and carrier compound. In some embodiments, the composition is comprised of at least 50%, 60%, 70%, 80%, 90%, or 95% sweetener polyol and carrier compound by weight. In some embodiments, the composition consists essentially of sweetener polyol and carrier compound. In some embodiments, the composition consists of sweetener polyol and carrier compound. In some embodiments, the composition is comprised of at least 10%, 20%, 30%, 40%, 50%, 60%, 70%, 80%, 90%, or 95% sweetener carbohydrate and/or sweetener polyol and carrier compound by weight. In some embodiments, the composition is comprised of at least 90% sweetener carbohydrate and/or sweetener polyol and carrier compound by weight. In some embodiments, the composition consists essentially of sweetener carbohydrate and/or sweetener polyol and carrier compound. In some embodiments, the composition consists of sweetener carbohydrate and/or sweetener polyol and carrier compound. In some embodiments, the composition does not comprise DNA, protein, lignin, or magnetic particles.

Further provided herein is a formulation comprising a sweetener composition. In some cases, the formulation is a syrup (i.e., a sweetener composition formulated as a syrup). A formulation can include water. A formulation can include a food additive. A formulation can include an artificial sweetener, a natural sugar substitute, or a combination thereof. An artificial sweetener can be one that is selected from the group consisting of: acesulfame potassium, advantame, alitame, aspartame, sodium cyclamate, dulcin, glucin, neohesperidin dihydrochalcone, neotame, P-4000, saccharin, aspartame-acesulfame salt, and sucralose. A natural sugar substitute can be one that is selected from the group consisting of: brazzein, curculin, glycyrrhizin, glycerol, inulin, mogroside, mabinlin, malto-oligosaccharide, mannitol, miraculin, monatin, monellin, osladin, pentadin, stevia, tagatose, and thaumatin. Any of the sweetener compositions, formulations, or consumable products described herein preferably have a reduced perceived bitterness as compared to the same product made using an artificial sweetener and/or a natural sugar substitute instead of a sweetener composition or made without a sweetener composition as described herein.

The sweetener compositions and formulations described herein can be used to make consumable products. Consumable products include food products, beverage products, pharmaceutical products, and hygiene products, as non-limiting examples. Food products include, but are not limited to, confectionary, chocolate, jam, ice cream, soup, whipped cream, baked goods, condiments, sauces, dairy products, and dressings. Beverage products include, but are not limited to, soft drink, flavored water, juice, sports drink, energy drink, alcoholic beverage, liqueur, carbonated beverage, caffeinated beverage, coffee, cocoa, tea, and dairy drinks. Pharmaceutical products include, but are not limited to, cough syrups, capsules, and tablets. Hygiene products include, but are not limited to, tooth paste and mouth wash. Other miscellaneous consumable products include, but are not limited to, chewing gum and spices.

In some cases, a consumable product may contain up to 0.1, 0.5, 1.0, 1.1, 1.2, 1.3, 1.4, 1.5, 1.6, 1.7, 1.8, 1.9, or 2.0% silica on a weight/weight basis. In some cases, the consumable product is less bitter than a control product, wherein the control product is identical to the consumable product and has the same sweetener carbohydrate and/or sweetener polyol but not formulated as a sweetener composition (i.e., with the carrier).

Additionally provided herein are methods to make a consumable product. Such methods comprise substituting a portion of a sweetener ingredient in a consumable product with a sweetener composition described herein. Additionally or alternatively, a sweetener composition can be added to the process of making the consumable product.

Also provided herein is a syrup sweetener composition comprising one or more sweetener carbohydrates and/or sweetener polyols and 6-12% carrier compound wt/wt relative to a sum of total sweetener carbohydrate and sweetener polyol; wherein the sweetener composition has enhanced sweetness compared to a control composition; and wherein the control composition consists of comparable contents to the sweetener composition but lacks the carrier compound. In some embodiments, the syrup comprises 8-10% carrier compound wt/wt relative to a sum of total sweetener carbohydrate and sweetener polyol.

Additionally provided herein are methods to make a consumable product. Such methods comprise substituting a portion of a sweetener ingredient in a with a sweetener composition described herein. Additionally or alternatively, a sweetener composition can be added to the process of making the consumable product.

Figure 1:
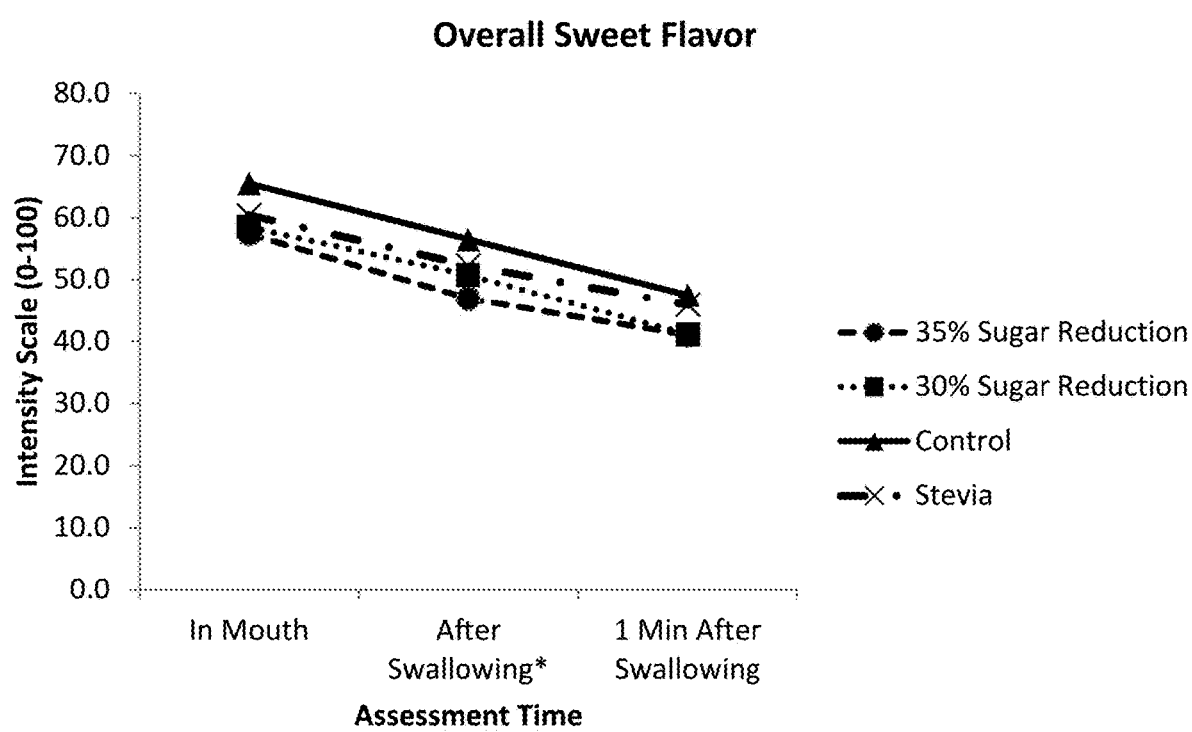
FIG. 1 shows overall sweet flavor intensity as a function of time for whipped double cream samples.

The novel features of the invention are set forth with particularity in the appended claims. A better understanding of the features and advantages of the present invention will be obtained by reference to the following detailed description that sets forth illustrative embodiments, in which the principles of the invention are utilized.

DETAILED DESCRIPTION OF THE INVENTION

Introduction

The present disclosure relates to sweetener compositions that can be used alone, formulated into sweetener composition formulations, or added to or further processed into a consumable product. The sweetener compositions herein comprise one or more sweetener carbohydrates and/or sweetener polyols and a carrier compound. The sweetener compositions herein may be sweeter in taste than a similar control composition (e.g., a composition comprising the same contents by identity and quantity as the sweetener composition but without the carrier compound).

Definitions

As used herein, the term "sweetener carbohydrate" refers to a consumable carbohydrate, which produces a sweet taste when consumed alone. A sweetener carbohydrate may be a monosaccharide or disaccharide. A sweetener carbohydrate may be a naturally-occurring carbohydrate. For example, it may be an isolated, purified sweetener. A sweetener carbohydrate may be a non-naturally occurring or synthetically-produced carbohydrate. Non-limiting examples of a sweetener carbohydrate include sucrose, glucose, maltose, lactose, high fructose corn syrup, and high maltose corn syrup. A sweetener carbohydrate may be sucrose, glucose, maltose, lactose, or a combination thereof. A sweetener carbohydrate may be sucrose, glucose, or a combination thereof. A sweetener carbohydrate may be sucrose. A sweetener carbohydrate may be glucose. A sweetener carbohydrate may be high fructose corn syrup, high maltose corn syrup, or a combination thereof. A sweetener carbohydrate may be high fructose corn syrup. A sweetener carbohydrate may be high maltose corn syrup.

As used herein, the term "sweetener polyol" refers to a consumable polyol which produces a sweet taste when consumed alone. Some non-limiting examples of sweetener polyols include xylitol, maltitol, erythritol, sorbitol, threitol, arabitol, hydrogenated starch hydrolysates (HSH), isomalt, lactitol, mannitol, and galactitol (dulcitol). In some instances, the polyol is a sugar alcohol. A sugar alcohol can be produced from a corresponding parent carbohydrate by any known method of reduction (via a chemical or biological transformation) of an acid or aldehyde to an alcohol. In some cases, a sweetener polyol can be created synthetically from a parent carbohydrate. In some cases, a sweetener polyol can be covalently attached to a carbohydrate (e.g. a monosaccharide, or di-saccharide). Alternatively or in combination, a sweetener polyol can be bio-derived or obtained from a biological source.

As used herein, the term "sweetener" or "sweetener ingredient" refers to a consumable product, which produces a sweet taste when consumed alone. Some non-limiting examples of a sweetener ingredient include a sweetener carbohydrate, sweetener polyol, artificial sweetener, and natural sugar substitute.

As used herein, the term "carrier compound" refers to a solid, food-grade material, which may be coated with a sweetener. A carrier compound through its large and active surface and structure may form hydrogen bonds or van der Waals bonds with a sweetener carbohydrate and/or sweetener polyol. As such, the carbohydrate and/or polyol can maintain its chemical integrity. For instance, the interaction between the carrier compound and the carbohydrate and/or polyol does not need to involve covalent bonds. The carrier compound may associate with the sweetener carbohydrate and/or sweetener polyol to provide characteristics different than a control composition, for instance enhanced sweetness, reduced bitterness, or reduced rate of dissolution. A carrier compound may be a solid composition lacking a distinctive taste. A carrier compound may be tasteless, flavorless, or odorless. Digestion of a carrier compound by a human may produce a low amount of usable calories. A carrier compound may be non-caloric. A carrier compound may at least partially dissolve in a solvent (e.g., water). A carrier compound optionally meets test requirements as described in the Food Chemicals Codex (FCC), the European Directive, or Japan's Specifications and Standards for Food Additives. Some non-limiting examples of a carrier compound are silica, silicon dioxide, chitosan, chitin, starch, maltodextrin, microcrystalline cellulose, hemicellulose, cyclodextrins, hydroxyalkyl cyclodextrins (e.g., hydroxypropyl and methyl cyclodextrins), inulin, pectin, carrageenans, titanium dioxide, magnesium oxide, magnesium hydroxide, calcium oxide, calcium carbonate, and natural gums (e.g., gum arabic, gellan gum, guar gum, locust bean gum, and xanthan gum). A carrier compound may be a combination of more than one distinct carrier compounds.

In some embodiments, a carrier compound comprises silica or silicon dioxide ($SiO_2$). In some embodiments, a carrier compound is silica or silicon dioxide ($SiO_2$). In some embodiments, a carrier compound is colloidal silica or silica particles. In some embodiments, a carrier compound is precipitated silica. In some embodiments, silica particles are particles comprising silica. In some embodiments, silica particles are particles consisting essentially of silica. In some embodiments, silica particles are particles consisting of silica.

A carrier compound can have an average particle size of up to 1, 2, 3, 4, 5, 7, 8, 9, 10, 11, 12, 13, 14, 15, 20, 25, 30, 35, 40, 45, 50, 55, 60, 65, 70, 75, 80, 85, 90, 95, or 100 microns. A carrier compound can have an average particle size of at least 1, 2, 3, 4, 5, 7, 8, 9, 10, 11, 12, 13, 14, 15, 20, 25, 30, 35, 40, 45, 50, 55, 60, 65, 70, 75, 80, 85, 90, 95, or 100 microns. A carrier compound can have an average particle size of about 1, 2, 3, 4, 5, 7, 8, 9, 10, 11, 12, 13, 14, 15, 20, 25, 30, 35, 40, 45, 50, 55, 60, 65, 70, 75, 80, 85, 90, 95, or 100 microns. In some embodiments, a carrier compound has an average particle size between 5 and 100, 10 and 80, 10 and 50, or 10 and 30 microns.

A carrier compound may have a high specific surface area. In some cases, a carrier compound may have a specific surface area of at least 20, 30, 40, 50, 60, 70, 80, 90, 100, 110, 120, 130, 140, 150, 160, 170, 180, 190, 200, 210, 220, 230, 240, 250, 260, 270, 280, 290, or 300 $m^2/g$. In some cases, a carrier compound may have a specific surface area of up to 20, 30, 40, 50, 60, 70, 80, 90, 100, 110, 120, 130, 140, 150, 160, 170, 180, 190, 200, 210, 220, 230, 240, 250, 260, 270, 280, 290, or 300 $m^2/g$. In some cases, a carrier compound may have a specific surface area of about 20, 30, 40, 50, 60, 70, 80, 90, 100, 110, 120, 130, 140, 150, 160, 170, 180, 190, 200, 210, 220, 230, 240, 250, 260, 270, 280, 290, or 300 $m^2/g$.

In some embodiments, a carrier compound is in a dehydrated state. For example, the decrease in mass upon drying of a carrier compound can be up to 1, 2, 3, 4, 5, 6, 7, 8, 9, or 10%. In some cases, a carrier compound can be annealed before being coated with one or more sweetener carbohydrates and/or sweetener polyols. In some cases, a carrier compound can be dried before being coated with one or more sweetener carbohydrates and/or sweetener polyols. In some cases, a carrier compound have moisture or water added to it before being coated with one or more sweetener carbohydrates and/or sweetener polyols. In some cases, a carrier compound can contain up to 0.001%, 0.005%, 0.01%, 0.05%, 0.1%, 0.5%, 1%, 1.5%, 2%, 2.5%, 3%, 3.5%, 4%, 4.5%, 5%, 5.5%, or 6% water wt/wt before being coated with one or more sweetener carbohydrates and/or sweetener polyols. In some cases, a carrier compound can contain at least 0%, 0.001%, 0.005%, 0.01%, 0.05%, 0.1%, 0.5%, 1%, 1.5%, 2%, 2.5%, 3%, 3.5%, 4%, 4.5%, 5%, 5.5%, or 6% water wt/wt before being coated with one or more sweetener carbohydrates and/or sweetener polyols. In some cases, a carrier compound can contain about 0%, 0.001%, 0.005%, 0.01%, 0.05%, 0.1%, 0.5%, 1%, 1.5%, 2%, 2.5%, 3%, 3.5%, 4%, 4.5%, 5%, 5.5%, or 6% water wt/wt before being coated with one or more sweetener carbohydrates and/or sweetener polyols. In some cases, a carrier compound can contain a moisture level or water content of 0-6%, 0-5%, 1-6%, 1-5%, 2-6%, 1-4%, 2-5%, 3-6%, 1-3%, 2-4%, 3-5%, or 4-6% wt/wt before being coated with one or more sweetener carbohydrates and/or sweetener polyols. In some cases, a carrier can be heated (e.g., at 400° C.) for at least 0.5, 1, 1.5, 2, 2.5, 3, 3.5, or 4 hours to remove moisture and dry the carrier.

As used herein, the term "solvent" refers to a liquid, which may be mixed with or used to dissolve a sweetener composition or one or more components of a sweetener composition. Non-limiting examples of a solvent include water, ethanol, and isopropanol. The solvent can be potable. The solvent can be water. Non-limiting examples of water include purified water, distilled water, double distilled water, deionized water, distilled deionized water, drinking water, well water, tap water, spring water, bottled water, carbonated water, mineral water, flavored water, or a combination thereof. A solvent may be a combination of two or more distinct solvents.

As used herein, the term "control composition" refers to a composition, to which a sweetener composition is compared. In some cases, a control composition comprises the one or more sweetener carbohydrates and/or sweetener polyols but not the carrier compound of the sweetener composition to which it is compared. In some cases, a control composition is formulated similarly to the sweetener composition. In some cases, a control composition is formulated identically to the sweetener composition. The control composition may comprise the same contents by identity and quantity as the one or more sweetener carbohydrates and/or sweetener polyols of a sweetener composition. In some cases, the one or more sweetener carbohydrates and/or sweetener polyols are in free, unassociated form. The control composition may consist of the same contents by identity and quantity as the one or more sweetener carbohydrates and/or sweetener polyols of a sweetener composition. The control composition may consist of the same contents by identity and quantity as the sweetener composition but without the carrier compound.

As used herein, the term "enhanced sweetness" or "higher perceived sweetness" refers to a stronger or higher sense of sweetness to a human. Sweetener compositions with enhanced sweetness taste sweeter than the control composition to which they are compared. A smaller amount (by weight or by volume) of a sweetener composition with enhanced sweetness may produce the same sense of sweetness as a larger amount (by weight or by volume) of a control composition that lacks enhanced sweetness. A sweetener composition with enhanced sweetness may produce a higher perceived sweetness and a lower caloric content than a control composition with a comparable amount (by weight) of the one or more sweetener carbohydrates and/or sweetener polyols in free, unassociated form. For example, 1.0 grams of a sweetener composition comprising about 0.08 grams of a carrier coated with about 0.92 grams of one or more sweetener carbohydrates and/or sweetener polyols may produce a higher perceived sweetness than a control composition that comprises about 0.92 grams of the one or more sweetener carbohydrates and/or sweetener polyols and does not comprise the carrier compound.

As used herein, the term "consumable product" refers to a product, which may be consumed (e.g., by eating, chewing, drinking, or swallowing). Consumable products include food products, beverage products, pharmaceutical products, and hygiene products, as non-limiting examples. Food products include, but are not limited to, confectionary, chocolate, jam, ice cream, soup, whipped cream, baked goods, condiments, sauces, dairy products, and dressings. Beverage products include, but are not limited to, soft drink, flavored water, juice, sports drink, energy drink, alcoholic beverage, liqueur, carbonated beverage, caffeinated beverage, coffee, cocoa, tea, and dairy drinks. Pharmaceutical products include, but are not limited to, cough syrups, capsules, and tablets. Hygiene products include, but are not limited to, tooth paste and mouth wash. Other miscellaneous consumable products include, but are not limited to, chewing gum and spices.

As used herein, the term "about" can be understood as within 10%, 9%, 8%, 7%, 6%, 5%, 4%, 3%, 2%, 1%, 0.5%, 0.1%, 0.05%, or 0.01% of the stated value.

In some cases, the term "portion" can be understood as about 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 99, 99.1, 99.2, 99.3, 99.4, 99.5, 99.6, 99.7, 99.8, 99.9, or 100% of the referenced value; at least 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 99, 99.1, 99.2, 99.3, 99.4, 99.5, 99.6, 99.7, 99.8, 99.9, or 100% of the referenced value; or up to 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 99, 99.1, 99.2, 99.3, 99.4, 99.5, 99.6, 99.7, 99.8, 99.9, or 100% of the referenced value.

In some cases, the term "one or more" can be understood as about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100; at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100; or up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100.

Sweetener Compositions

A sweetener composition comprises one or more sweetener carbohydrates and/or sweetener polyols and a carrier compound. In some cases, a sweetener composition comprises one or more sweetener carbohydrates and a carrier compound. In some cases, a sweetener composition comprises one or more polyols and a carrier compound. In some cases, a sweetener composition does not contain a sweetener carbohydrate. In some cases, a sweetener composition does not contain a sweetener polyol. A sweetener composition can be purified or isolated. A sweetener composition is preferably substantially uniform or homogenous. A sweetener composition can be in the form of a solid (e.g., a powder) or a syrup. In some cases, a sweetener composition is dry and/or dehydrated. In some cases, a sweetener composition can be in a solvent (e.g., water).

The sweetener composition herein can have a defined ratio of amounts of the carrier compound and the one or more sweetener carbohydrates and/or sweetener polyols. Such a ratio of amounts can be determined by mass, weight, volume, mole, or a combination thereof. In some examples, a ratio of the carrier compound to a sum of total sweetener carbohydrate and sweetener polyol can be at least 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, or 12.0%. In other examples, a ratio of the carrier compound to a sum of total sweetener carbohydrate and sweetener polyol can be up to 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, or 12.0%. In other examples, a ratio of the carrier compound to a sum of total sweetener carbohydrate and sweetener polyol can be about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0%. In other examples, a ratio of the carrier compound to a sum of total sweetener carbohydrate and sweetener polyol can be between about 4.0-12.0%, 5.0-12.0%, 6.0-12.0%, 7.0-12.0%, 8.0-12.0%, 6.0-11.0%, 6.0-10.0%, 6.0-9.0%, 6.0-8.0%, 7.0-11.0%, 7.0-10.0%, or 7.0-9.0%. A ratio of the carrier compound to a sum of total sweetener carbohydrate and sweetener polyol can be about 6.0-12.0%.

A sweetener composition may have enhanced sweetness compared to a control composition. Preferably, the control composition is the one or more sweetener carbohydrates and/or sweetener polyols but not the carrier compound of the sweetener composition to which it is compared.

The sweetener composition can have a quantified enhanced sweetness. Such enhanced sweetness may be determined by a sensory test. Examples of sensory taste tests are described herein.

In some instances, a sweetener composition can have the sweetness enhanced by at least 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control composition. The sweetener composition can have the sweetness enhanced by up to 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control composition. the sweetener composition can have the sweetness enhanced by about 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control composition. For example, the sweetness can be enhanced by 10-80%, 20-70%, or 40-60% relative to a control composition.

In some cases when the carrier compound is silica, the sweetness of a sweetener composition can have a ratio of silica to sweetener carbohydrate and/or sweetener polyol that gives a maximum sweetness. Increasing the amount of silica relative to sweetener carbohydrate and/or sweetener polyol beyond the maximum point can decrease the sweetness of the composition. In some cases, wherein the amount of silica is higher than the maximum sweetness amount, a grainy, sandy, or chalky characteristic can enter the taste profile. In some cases, when the amount of silica is less than the maximum sweetness amount, the composition does not fully benefit from the sweetness enhancement effect of the silica. In some cases, the maximum sweetness amount is between about 6-12% carrier compound (wt/wt relative to the sweetener carbohydrate and/or sweetener polyol). In some cases, the maximum sweetness amount is between about 8-10% carrier compound (wt/wt relative to the sweetener carbohydrate and/or sweetener polyol). In some cases, the maximum sweetness amount is about 8% carrier compound (wt/wt relative to the sweetener carbohydrate and/or sweetener polyol).

The physical properties of a sweetener composition, sweetener composition formulation, or its individual components can be characterized, e.g., by elemental analysis, viscosity, microscopy, elemental mapping, transmission Fourier transform infrared spectroscopy (FTIR), or dynamic light scattering (DLS). For example, the compositions can be powders with small particle sizes. The particle sizes of a sweetener composition can be measured (e.g., by DLS). The distribution of particle sizes can be measured by size fractionation of particles using sieves with openings of different sizes. Physical properties of a sweetener composition may affect its taste properties. For example, the perceived sweetness of a sweetener composition may be correlated to the distribution of particle sizes. In some cases, at least 10, 20, 30, 40, 50, 60, 70, 80, or 90 percent of the particles of the compositions described herein are between about 25 microns and about 200 microns in diameter. In some cases, at least 10, 20, 30, 40, 50, 60, 70, 80, or 90 percent of the particles of the compositions described herein are less than or equal to 74 microns in diameter. In some cases, at least 10, 20, 30, 40, 50, 60, 70, 80, or 90 percent of the particles of the compositions described herein are at least 25 microns in diameter. In some cases, at least 10, 20, 30, 40, 50, 60, 70, 80, or 90 percent of the particles of the compositions described herein are between about 25 microns and about 74 microns in diameter.

Methods of Making Sweetener Compositions

In one instance, a method of producing a sweetener composition comprises mechanically coating a carrier compound with one or more sweetener carbohydrates and/or sweetener polyols. For example, the method of producing a sweetener composition can comprise mechanically coating the carrier compound silica with one or more sweetener carbohydrates and/or sweetener polyols. Each of the one or more sweetener carbohydrates and/or sweetener polyols and carrier compound can be added simultaneously or sequentially in any order. A carrier compound can be coated with one or more sweetener carbohydrates and/or sweetener polyols by one or more mechanical methods. The mechanical coating can be accomplished by one or more methods including stirring, grinding, compressing, blending, agitating, rotational mixing, solid-solid mixing with a static mixer, mortar and pestle, Kenics mixing, drum tumbling, and Turbula mixing. In some cases, two or more forms of mechanical methods can be used in series or in parallel. For example, in some cases, one or more sweetener carbohydrates and/or sweetener polyols and one or more carrier compounds can be mixed together, ground mechanically in a grinder, and subsequently further ground mechanically via a mortar and pestle to achieve coating of the carrier.

The conditions of the mechanical coating or grinding (e.g., temperature, time duration, speed, timing, rate, force, pressure, etc.) can affect the sweetness of the resulting composition. In some cases, these conditions are selected to give the largest enhancement of sweetness to the resulting composition. In some cases, grinding is carried out for up to 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. In some cases, the grinding can be carried out for at least 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. In some cases when two or more forms of mechanical methods are used in series or in parallel, the timing and conditions of each form can be selected independently.

In some cases, a carrier compound can be coated with one or more sweetener carbohydrates and/or sweetener polyols by preparing a dry formulation without using water. For example, one or more sweetener carbohydrates and/or sweetener polyols and a carrier compound can be mixed to form a powder and then subsequently ground together to form hydrogen bonds between the sweetener coating and the carrier compound. In some cases, the dry grinding can form a substantially homogenous solid powder mixture. In one example, a method of producing a sweetener composition comprises mixing one or more sweetener carbohydrates and/or sweetener polyols and a carrier compound without adding water, grinding the mixture of solids in a mechanical grinder, grinding the mixture in a mortar and pestle, passing the composition through a sieve with a mesh having an opening between about 40 and about 100 mesh, and subsequently sonicating the mixture for at least 5 min.

In some cases, a sweetener composition is produced by mixing or dissolving the carrier compound and/or one or more sweetener carbohydrates and/or sweetener polyols in a solvent. In some cases, individual components may be mixed or dissolved in the same or different solvents. A carrier compound, a solvent, and one or more sweetener carbohydrates and/or sweetener polyols can be mixed together in any order, separately, alternately, simultaneously, or a combination thereof. Each of the carrier compound and/or one or more sweetener carbohydrates and/or sweetener polyols may be mixed with a solvent in any order separately, alternately, simultaneously, or a combination thereof (e.g., mixing one or more sweetener carbohydrates and/or sweetener polyols with a solvent and then adding a carrier compound; mixing a carrier compound with a solvent and then adding one or more sweetener carbohydrates and/or sweetener polyols; or mixing one or more sweetener carbohydrates and/or sweetener polyols and a carrier compound with a solvent). In one example, a method to form a sweetener composition comprises mixing one or more sweetener carbohydrates (i.e. sucrose) and/or sweetener polyols with water at 70° C. in a ratio of 65/35 carbohydrate/water wt/wt, slowly adding a carrier compound (i.e. silica) up to 8% wt/wt relative to the sum of sweetener carbohydrates (i.e. sucrose) and/or sweetener polyols to form a syrup of sweetener coated carrier, and sonicating the syrup.

During mixing, one or more reaction parameters such as temperature, concentration, stoichiometry, reaction time, order of mixing, mixing speed, mixing time, and pH can be adjusted. Adjusting one or more reaction parameters may affect the molecular structure, porosity, density, and/or particle size of the carrier compound that is formed.

The concentration of one or more sweetener carbohydrates and/or sweetener polyols mixed or dissolved in a solvent can be adjusted. The concentration of one or more sweetener carbohydrates and/or sweetener polyols mixed or dissolved in a solvent may be at least 5%, 10%, 15%, 20%, 25%, 30%, 35%, 40%, 45%, 50%, 55%, 60%, 65%, 70%, 75%, 80%, 85%, 90%, or 95% by weight. The concentration of one or more sweetener carbohydrates and/or sweetener polyols mixed or dissolved in a solvent may be up to 5%, 10%, 15%, 20%, 25%, 30%, 35%, 40%, 45%, 50%, 55%, 60%, 65%, 70%, 75%, 80%, 85%, 90%, or 95% by weight. The concentration of one or more sweetener carbohydrates and/or sweetener polyols mixed or dissolved in a solvent may be about 5%, 10%, 15%, 20%, 25%, 30%, 35%, 40%, 45%, 50%, 55%, 60%, 65%, 70%, 75%, 80%, 85%, 90%, or 95% by weight. In some cases, the concentration of one or more sweetener carbohydrates and/or sweetener polyols mixed or dissolved in a solvent is between about 10-70%, 15-70%, 15-65%, 20-65%, 20-60%, 20-50%, 20-40%, or 20-30%. In some cases, the concentration of one or more sweetener carbohydrates and/or sweetener polyols mixed or dissolved in a solvent is about 20%. In some cases, the concentration of one or more sweetener carbohydrates and/or sweetener polyols mixed or dissolved in a solvent is about 30%. In some cases, the concentration of one or more sweetener carbohydrates and/or sweetener polyols mixed or dissolved in a solvent is about 65%.

A carrier compound and one or more sweetener carbohydrates can be mixed by using a solvent or volatile liquid. For example, a carrier compound and one or more sweetener carbohydrates and/or sweetener polyols can be mixed by using a solvent or volatile liquid to form a paste that can be dried to obtain a solid. In some embodiments, a carrier compound and one or more sweetener carbohydrates and/or sweetener polyols can be mixed by using a solvent or volatile liquid to form a substantially uniform paste that can be dried to obtain a substantially uniform solid. In some embodiments, the solvent or volatile liquid can be water or iso-propanol for example.

Formulations of Sweetener Compositions

A sweetener composition may be formulated as a syrup. In some cases, the ratio of total sweetener carbohydrates and/or sweetener polyols to solvent in a sweetener composition formulation is at least 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In some cases, the ratio of total sweetener carbohydrates and/or sweetener polyols to solvent in a sweetener composition formulation is up to 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In some cases, the ratio of total sweetener carbohydrates and/or sweetener polyols to solvent in a sweetener composition formulation is about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5.

The sweetener compositions herein can be added to or mixed with one or more food additives. Food additives can add volume and/or mass to a sweetener composition. The sweetener compositions herein may be mixed with food additives such that up to 0.001, 0.005, 0.01, 0.05, 0.1, 0.5, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99 weight % of the sweetener composition formulation is food additives. The sweetener compositions herein may be mixed with food additives such that at least 0.001, 0.005, 0.01, 0.05, 0.1, 0.5, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99 weight % of the sweetener composition formulation is food additives. The sweetener compositions herein may be mixed with food additives such that about 0.001, 0.005, 0.01, 0.05, 0.1, 0.5, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99 weight % of the sweetener composition formulation is food additives. Some non-limiting examples of a food additive include food coloring, natural flavoring, artificial flavoring, batch marker, food stabilizer, food acid, filler, anticaking agent, antioxidant, bulking agent, color retention agent, emulsifier, humectant, thickener, pharmaceutical excipient, solid diluent, acid salt, alkali salt, organic salt, inorganic salt, nutrient (e.g., macronutrient, micronutrient, essential nutrient, non-essential nutrient, dietary fiber, amino acid, vitamin, dietary mineral), sweetener, artificial sweetener, natural sugar substitute, and preservative, for example. Some non-limiting examples of food additives are silica, silicon dioxide, cellulose, microcrystalline cellulose, powdered cellulose, starch, modified food starch, amylum, calcium carbonate, maltodextrin, hemicellulose, cyclodextrins, hydroxyalkyl cyclodextrins, inulin, pectin, chitin, chitosan, carrageenans, agar, natural gums (e.g., gum arabic, gellan gum, guar gum, locust bean gum, and xanthan gum), and magnesium stearate. Some non-limiting examples of an artificial sweetener are acesulfame potassium, advantame, alitame, aspartame, sodium cyclamate, dulcin, glucin, neohesperidin dihydrochalcone, neotame, P-4000, saccharin, aspartame-acesulfame salt, and sucralose. Some non-limiting examples of natural sugar substitutes are brazzein, curculin, glycyrrhizin, glycerol, inulin, mogroside, mabinlin, malto-oligosaccharide, mannitol, miraculin, monatin, monellin, osladin, pentadin, stevia (including partly stevia components), tagatose, and thaumatin. In some cases, a food additive differs from a sweetener carbohydrate or sweetener polyol, as food additives do not coat the carrier compound. In some cases, a compound can function as one or more of a carrier compound, a food additive, and a sweetener carbohydrate or sweetener polyol. A food additive may be a combination of two or more distinct food additives. In some cases, the sweetener composition and/or sweetener composition formulation does not comprise DNA, protein, lignin, and/or magnetic particles.

At least 5, 10, 15, 20, 25, 30, 35, 40, 45, 50, 55, 60, 65, 70, 75, 80, 85, 90, 95, 96, 97, 98, 99, 99.5, 99.9, or 100% of the sweetener composition formulation by weight may be one, two, three, four, or five components selected from the group consisting of sweetener carbohydrate, sweetener polyol, carrier compound, solvent, and food additive. Up to 5, 10, 15, 20, 25, 30, 35, 40, 45, 50, 55, 60, 65, 70, 75, 80, 85, 90, 95, 96, 97, 98, 99, 99.5, 99.9, or 100% of the sweetener composition formulation by weight may be one, two, three, four, or five components selected from the group consisting of sweetener carbohydrate, sweetener polyol, carrier compound, solvent, and food additive. About 5, 10, 15, 20, 25, 30, 35, 40, 45, 50, 55, 60, 65, 70, 75, 80, 85, 90, 95, 96, 97, 98, 99, 99.5, 99.9, or 100% of the sweetener composition formulation by weight may be one, two, three, four, or five components selected from the group consisting of sweetener carbohydrate, sweetener polyol, carrier compound, solvent, and food additive.

Methods of Making and/or Formulating Sweetener Compositions and/or Sweetener Composition Formulations A method of making and/or formulating a sweetener composition and/or sweetener composition formulation may comprise drying and/or concentrating. In some cases, drying forms a dry and/or dehydrated sweetener composition and/or sweetener composition formulation. In some cases, drying forms a solid sweetener composition and/or sweetener composition formulation. In some cases, concentrating forms a concentrated sweetener composition and/or sweetener composition formulation. Some non-limiting examples of drying methods include thermal drying, evaporation, distillation, boiling, heating in an oven, vacuum drying, spray drying, freeze drying, lyophilization, or a combination thereof. The mechanism of drying can affect the hydration and molecular structure of the sweetener composition and/or formulation thus giving rise to sweetener compositions and/or formulations with different physical properties. The sweetener composition and/or sweetener composition formulation can be dried until the composition and/or formulation comprises up to 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, or 80% solvent (e.g., water) by weight. The sweetener composition and/or sweetener composition formulation can be dried until the composition and/or formulation comprises at least 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, or 80% solvent (e.g., water) by weight. The sweetener composition and/or sweetener composition formulation can be dried until the composition and/or formulation comprises about 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, or 80% solvent (e.g., water) by weight. For example, a sweetener composition formulated as a syrup can be dried via any standard drying method (e.g., 12-80 hours in an oven at 60° C.) to remove a solvent to form a dry solid sweetener composition and/or sweetener composition formulation. In another example, a sweetener composition formulated as a syrup can be concentrated (e.g., from a syrup with 80% water to a syrup with 35% water).

A method of making and/or formulating a sweetener composition and/or sweetener composition formulation may comprise diluting and/or hydrating. In some cases, the diluting may comprise addition of a solvent. The sweetener composition and/or sweetener composition formulation can be diluted until the composition and/or formulation comprises up to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99, 99.5, or 99.9% solvent by weight. The sweetener composition and/or sweetener composition formulation can be diluted until the composition and/or formulation comprises at least 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99, 99.5, or 99.9% solvent (e.g., water) by weight. The sweetener composition and/or sweetener composition formulation can be diluted until the composition and/or formulation comprises around 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99, 99.5, or 99.9% solvent (e.g., water) by weight. For example, a sweetener composition formulated as a syrup can be diluted (e.g., from a syrup with 35% water to a syrup with 80% water). In another example, a dry sweetener composition can be hydrated (e.g., from a dry solid to a syrup with 80% water).

A method of making and/or formulating a sweetener composition and/or sweetener composition formulation may comprise mechanical mixing or grinding. A sweetener composition, sweetener composition formulation, individual component (e.g., sweetener carbohydrate, sweetener polyol), intermediate, and/or mixture can be mixed or ground by one or more mechanical methods. Non-limiting examples of mechanical methods include stirring, grinding, compressing, blending, agitating, rotational mixing, solid-solid mixing with a static mixer, mortar and pestle, Kenics mixing, drum tumbling, and Turbula mixing. In some cases, two or more forms of mechanical methods can be used in series or in parallel. For example, a sweetener composition and/or sweetener composition formulation can be ground mechanically in a grinder and subsequently further ground mechanically via mortar and pestle. The conditions of the mechanical coating or grinding (e.g., temperature, time duration, speed, timing, rate, force, pressure, etc.) can affect the sweetness of the resulting composition and/or formulation. These conditions may be selected to give the largest enhancement of sweetness to the resulting composition and/or formulation. Mixing or grinding may be carried out for at least 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. Mixing or grinding may be carried out for up to 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. Mixing or grinding may be carried out for about 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. In some cases when two or more forms of mechanical methods are used in series or in parallel, the timing and conditions of each form can be selected independently.

A method of making and/or formulating a sweetener composition and/or sweetener composition formulation may comprise sonicating. A sweetener composition, sweetener composition formulation, individual component (e.g., sweetener carbohydrate, sweetener polyol), intermediate, and/or mixture can be subjected to sonication. The sonication can be for up to 1, 2, 3, 4, 5, 6, 7, 8, 9, 10, 12, 14, 16, 20, 24, 30, 40, 50, or 60 min. The sonication can be for at least 1, 2, 3, 4, 5, 6, 7, 8, 9, 10, 12, 14, 16, 20, 24, 30, 40, 50, or 60 min. The sonication can be for about 1, 2, 3, 4, 5, 6, 7, 8, 9, 10, 12, 14, 16, 20, 24, 30, 40, 50, or 60 min. The sonication may occur with heating. The sonication may occur at a temperature of up to 25, 30, 35, 40, 45, 50, 55, 60, 65, 70, 75, 80, 85, 90, 95, or 100° C. The sonication may occur at a temperature of at least 25, 30, 35, 40, 45, 50, 55, 60, 65, 70, 75, 80, 85, 90, 95, or 100° C. The sonication may occur at a temperature of around 25, 30, 35, 40, 45, 50, 55, 60, 65, 70, 75, 80, 85, 90, 95, or 100° C. The sonication may occur at room temperature. In some cases, the sonication occurs during grinding or mixing. In some cases, the sweetener composition and/or sweetener composition formulation is sonicated. In some cases, the sweetener composition and/or sweetener composition formulation is not sonicated.

A method of making and/or formulating a sweetener composition and/or sweetener composition formulation may comprise filtering and/or sieving. A sweetener composition, sweetener composition formulation, individual component (e.g., sweetener carbohydrate, sweetener polyol), intermediate, and/or mixture can be passed through a sieve or sieving tower to remove particles of particular sizes, of at least a minimum size, of at most a maximum size, or of at least a minimum size and at most a maximum size from the composition. The sieve can have a mesh with openings up to 30, 40, 50, 60, 70, 80, 90, 100, 110, 120, 130, 140, 150, 160, 170, 180, 190, or 200 mesh. The sieve can have a mesh with openings of at least 30, 40, 50, 60, 70, 80, 90, 100, 110, 120, 130, 140, 150, 160, 170, 180, 190, or 200 mesh. The sieve can have a mesh with openings around 30, 40, 50, 60, 70, 80, 90, 100, 110, 120, 130, 140, 150, 160, 170, 180, 190, or 200 mesh. The sieve can have a mesh with openings of about 40 to about 100 mesh. The sieve can have a mesh with openings of about 60 to about 70 mesh.

A method of making and/or formulating a sweetener composition and/or sweetener composition formulation may comprise isolating or purifying.

Applications of Sweetener Compositions

A sweetener composition provided herein may be used as a sweetener for a consumable product. A consumable product may comprise a composition provided herein. Some non-limiting examples of a consumable product include food products, beverage products, pharmaceutical products, and hygiene products.

The consumable product may contain silica. The consumable product may contain up to 0.0001, 0.0005, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% silica weight/weight. The consumable product may contain at least 0.0001, 0.0005, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% silica weight/weight. The consumable product may contain about 0.0001, 0.0005, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% silica weight/weight.

The consumable product may have an acidic pH. In some cases, the consumable product may have a pH of at least 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9. In some cases, the consumable product may have a pH of up to 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9. In some cases, the consumable product may have a pH of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9.

A method of producing a consumable product with enhanced sweetness, lower caloric value, reduced bitterness, or a combination thereof may comprise adding a sweetener composition and/or sweetener composition formulation to the consumable product or substituting a portion of one or more sweetener ingredients in the consumable product with a sweetener composition and/or formulation. The sweetener composition and/or formulation may reduce the perceived bitterness of a consumable product. The sweetener compositions and/or formulations described herein can function as bitterness reducers and, in some instances, as bitterness masking agents. For example, adding a sweetener composition and/or formulation described herein to a consumable product can reduce or mask a bitter taste. A sweetener composition and/or formulation as described herein can reduce the bitterness of a medicine or pharmaceutical. For example, a method of reducing bitterness in a medicine or pharmaceutical can comprise adding a sweetener composition and/or formulation described herein to the medicine or pharmaceutical. Reducing the bitterness of a medicine can have the beneficial effect of increasing patient compliance and desire to take a medicine, particularly with pediatric patients. In some cases, a consumable product may comprise one or more modifying components that allow for incorporation of the sweetener composition and/or formulation.

A sweetener composition and/or sweetener composition formulation described herein can be added to or substituted into (e.g., by replacing a portion of one or more sweetener ingredients in the consumable product) a consumable product to produce at least 1, 2, 3, 4, 5, 6, 7, or 8; up to 1, 2, 3, 4, 5, 6, 7, or 8; or about 1, 2, 3, 4, 5, 6, 7, or 8 of the characteristics selected from the group consisting of increased sweetness, reduction of sweetener used while maintaining sweetness sensation, increased creamy aftertaste, decreased bitter aftertaste, decreased mouth drying aftereffect, decreased metallic aftertaste, decreased liquorice aftertaste, and reduced caloric value of the consumable product. The characteristic of the consumable product comprising the sweetener composition and/or formulation can be compared to a control product that does not have the sweetener composition and/or formulation added to it or substituted into it. For example, a consumable product with an added or substituted sweetener composition and/or formulation can have one or more of the characteristics enhanced by at least 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control product. A consumable product with an added or substituted sweetener composition and/or formulation can have one or more of the characteristics enhanced by up to 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control product. A consumable product with an added or substituted sweetener composition and/or formulation can have one or more of the characteristics enhanced by about 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control product. For example, the sweetness can be enhanced by 10-80%, 20-70%, or 40-60%.

Sensory Testing

Enhanced sweetness can be determined by a sensory test. Equivalent sweetness with a lower caloric value can be determined by a sensory test. The sensory test may be a taste test. The sensory test may be a blind test. One non-limiting example of a taste test method to measure enhanced sweetness is to taste a set amount of a control composition, and then taste varying amounts of the sweetener composition to find the amount of sweetener composition that corresponds to the sweetness of the control composition. The enhanced sweetness can be calculated by the following formula: [amount of control composition−amount of sweetener composition required for equal sweetness]/[amount of control composition]. For example, varying amounts of a sweetener composition described herein (e.g., 5, 4, 3, 2 and 1 mg of a composition comprising 65% sucrose and 1% silica) are tasted to find an equal sweetness to a control composition (e.g., 5 mg sucrose). In this case, if the test shows that 3 mg of the sweetener composition has an equivalent sweetness to 5 mg of the control composition, then the enhanced sweetness is calculated as (5-3)/5=40%.

A sensory test can use one or more various protocols. For example, a sensory test can be the "triangle method", follow ISO requirements, or a combination thereof. The taste test can be the average of multiple trials. For example, each taste tester can consume multiple sweetener compositions or foods, beverages, or consumable products comprising a sweetener composition and sequence them by relative sweetness. A taste test can comprise tasting a standard and determining whether a tested composition is more or less sweet than the standard.

A taste test may be a screening test, a professional taste test, or a market research test. A screening test may be performed by at least 1, 2, 3, 4, 5, 6, 7, 8, or 9 taste testers. A professional taste test may be performed by at least 10, 15, 20, 25, or 30 taste testers. A market research test may be performed by at least 31, 40, 50, 60, 70, 80, 90, 100, 150, 200, 300, 400, or 500 taste testers. A taste tester can be a person with average taste perception. A taste tester can be a professional taste tester. A taste tester can be a person who has passed a tasting exam by correctly identifying foods or food components. A taste tester can be a person who can identify the relative amounts of a taste or flavor (e.g., correctly sequence varying amounts of sugar in water).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Formation of a Sweetener Composition

Sucrose (80 g., pure, food-grade) and silica (6.4 g., Perkasil® SM 660, pure, food-grade, produced by W. R. Grace & Co) are combined in a Moulinex® coffee grinding machine. The solids are ground together for 20 sec to form a powder (8% silica wt/wt in sucrose). The solids are transferred to an electric mortar and pestle. The upper pestle pressure is set at a scale reading of 6.5. The scraper is adjusted as closed 6.5 rounds from minimal contact with the mortar side. The contact of the pestle with the mortar side is adjusted as closed 11.5 rounds from minimal contact. The mixture is ground for 5 minutes using the mortar and pestle. The combined powdered mixture is optionally sonicated for 30 min at 40° C. at 40 KHz. The mixture is then passed through a sieve (70 mesh) to remove larger particles. The powder that passes through the sieve is labeled as composition S1.

Example 2: Size Fractionation of Sweetener Compositions

Size fractionation is performed on the composition S1 of Example 1 by passing the composition through sieves with successively smaller openings to determine the particle size distribution of the composition as shown in Table 2.

TABLE 2

| Size Range (micron) | % Weight |
|---|---|
| 74-200 | 23 |
| 53-74 | 8 |
| 37-53 | 12 |
| 25-37 | 39 |
| <25 | 18 |

Example 3: Formation of Sweetener Compositions

A) 8% silica in sucrose—powder preparation: Silica (4.0 g., Perkasil® SM 660, pure, food-grade) is transferred into a mechanical grinder and ground for 20 sec. The silica is then transferred into a mortar and pestle for further grinding for 10 min. Sucrose (50 g., pure, food-grade) is ground in a mechanical grinder (Moulinex® grinder) for 20 sec. The sucrose is added in portions to the mortar and pestle for further grinding with the silica for 10 min. Once all the sucrose is added, the mixture is ground for 5 more minutes using the mortar and pestle. The combined powdered mixture is sonicated for 30 min at 40° C. then put through a sieve (70 mesh) to remove larger pieces. The powder that passed through the sieve is labeled as composition 3A.

B) 8% silica in sucrose syrup: Sucrose (70 g, pure, food-grade) is transferred into a mechanical grinder and ground for 20 sec. The ground sugar is transferred into a mortar and pestle for another 10 min of grinding. The ground sample is transferred in portions into 37.7gr deionized water previously heated to 70° C. (while stirring) until a clear yellowish solution is achieved (yielding a solution of 65:35 ratio between sucrose and water). Silica (5.6 g, Perkasil® SM 660, pure, food-grade, 8% relative to sucrose) is added to the sucrose syrup in portions (while stirring). The resulting solution is stirred vigorously for 10 more minutes. The dispersion is sonicated at 40° C. for 30 min and labeled as composition 3B.

C) Sucrose syrup: 70 gr of sucrose ground mechanically and physically, are transferred in portions to 37.7 gr deionized water previously heated to 70° C. A clear yellowish solution is achieved (65:35 ratio between sucrose and water). The clear solution is stirred vigorously for 10 more minutes. The dispersion is sonicated at 40° C. for 30 min and labeled as composition 3C.

Example 4: Tasting Sweetener Compositions of Example 3

Three testers are each given two sets of triangle tests to taste the sweetener compositions. The results are displayed in the tables herein. The "+" is the label for the sample with the highest perceived sweetness.

Test 4A (powders): Each tester is given 4 mg of the following powdered samples: Pure sucrose and 3A.

TABLE 4A

| | Test 1 | | | Test 2 | | |
|---|---|---|---|---|---|---|
| Sample: | sucrose | 3A | sucrose | sucrose | 3A | 3A |
| Taster 1 | + | | | | | + |
| Taster 2 | + | | | | | + |
| Taster 3 | | + | | | + | + |

Test 4B (syrups): Each tester is given 4 mg of the following syrup samples: 3B and 3C.

TABLE 4B

| | Test 1 | | | Test 2 | | |
|---|---|---|---|---|---|---|
| | 3B | 3C | 3C | 3C | 3B | 3B |
| Taster 1 | + | | | | | + |
| Taster 2 | + | | + | + | | + |
| Taster 3 | + | | | | + | + |

Test 4C (solutions): Each tester is given about 5 ml taken from two stock samples: i) 10 g of sucrose in 500 mL deionized water and ii) 10 g of 3A in 500 mL deionized water.

TABLE 4C

| | Test 1 | | | Test 2 | | |
|---|---|---|---|---|---|---|
| Sample: | sucrose | sucrose | 3A | sucrose | 3A | 3A |
| Taster 1 | | + | + | | + | + |
| Taster 2 | | + | + | + | + | |
| Taster 3 | | | + | | + | + |

Example 5: Formation of Chocolate Comprising Enhanced Sweetener Compositions The sample chosen as the enhanced sucrose added in all cream preparation is composition 3A (described in example 3-8% Perkasil® in sucrose, dry preparation). Dark chocolate with no added sugar by "Galler chocolatier" (25 g) is slowly melted in a hot water bath. As the chocolate melted, about 7 gr of milk is added in portions until a creamy soft texture is reached. The sweetener or sugar is added to the melted chocolate and stirring continued. The mixture is cooled to room temperature. The compositions of Chocolate 5A-5D are made of ingredients as depicted in the following table:

| Ingredients | Chocolate 5A | Chocolate 5B | Chocolate 5C | Chocolate 5D |
|---|---|---|---|---|
| Chocolate | 25 | 25 | 25.258 | 25.267 |
| Milk | 7 | 7 | 7.022 | 7.023 |
| sweetener | None | Sucrose - 25 mg | 3 A - 20 mg | 3A - 25 mg |

Example 6: Taste Test of Chocolate Compositions of Example 5

Three taste testers are given a small sample from 4 types of chocolate. The details of the chocolate preparation are described in Example 5. The results of the taste test are described in Table 6.

TABLE 6

|  | Chocolate 5A | Chocolate 5B | Chocolate 5C | Chocolate 5D |
|---|---|---|---|---|
| Tester 1 | Bitter and slightly sweet | Sweeter slightly less bitter | Not as bitter and sweeter | The sweetest sample Weak bitterness |
| Tester 2 | Bitter and slightly sweet | Sweeter slightly less bitter | Not as bitter and sweeter Has a bit of an unpleasant lingering | Same as previous, less of the lingering sensation Very similar to the previous sample |
| Tester 3 | Bitter and slightly sweet | Sweeter slightly less bitter | Not as bitter and sweeter | The sweetest sample Weak bitterness |

Example 7: Formation and Tasting of Bitterness Reduced Paracetamol

A tablet of a known bitter medicine, paracetamol ("Acamol™" by Teva, also known as acetaminophen) is crushed. Several 3 mg portions of the crushed medicine are weighed in separate dishes. A drop of about 10 mg sweetener is added to each portion. This is repeated both with two sweetener syrups: i) sucrose syrup (65 g sucrose in 35 g water) and ii) enhanced syrup (7 g Perkasil® added to a syrup of 65 g sucrose in 35 g water at 75° C.). The results are disclosed in Table 7.

TABLE 7

| Taster | Paracetamol + sucrose syrup | Paracetamol + enhanced sucrose syrup |
|---|---|---|
| Tester 1 | Very bitter No sweetness | Less bitter, sweeter, A huge difference |
| Tester 2 | Extremely bitter | The sample is still bitter but significantly less and sweeter |
| Tester 3 | Extremely bitter | The sample is still bitter but significantly less and sweeter |

Example 8: Formation of Sweetener Compositions Comprising Chitosan Carrier Compound Chitosan (Kiofine® B, 50µ particle size) is used in the preparation of the following samples:

A) 8% Chitosan in sucrose dry sample: 15gr of sucrose are transferred into a mechanical grinder, 1.2 gr (8%) of chitosan is added, the mixture is ground for 20 sec. After a sample is taken, the mixture is transferred into a mortar and pestle for another 10 min of grinding. A sample is taken from the ground mixture. The remaining ground mixture is sonicated for 30 min at 40° C. The sample is passed through a sieved and labeled 8A.

B) 8% Chitosan in sucrose syrup where the dry mixed powder is added to water at 70° C. 6 g of the sieved and ground mixture of chitosan in sucrose (from compound 8A) is transferred in portions to 3 gr of deionized water at 70° C. The dispersion is stirred vigorously for about 10 min. The dispersion is sonicated at 40° C. for 30 min. The resulting chitosan syrup is opaque and with a dark orange color. The resulting starch syrup is opaque and white. A sample of the starch syrup is dried in an oven at 90° C. for 72 hours and labeled 8B.

C) 8% Chitosan in sucrose syrup where the Chitosan is added to the sucrose syrup. 10 g of sucrose (ground mechanically and manually) is transferred in portions into 5.4 g deionized water previously heated to 70° C. (while stirring) until a clear yellowish solution is achieved (yielding a solution of 65:35 ratio between sucrose and water). 0.8 gr (8%) of chitosan is added to the sucrose syrup in portions (while stirring). The resulting dispersion is stirred vigorously for 20 more minutes. Following stirring, the solution is sonicated at 40° C. for 30 min. The resulting syrup is opaque and with a dark orange color. The resulting starch syrup is opaque and white. A sample of the chitosan syrup is dried in an oven at 90° C. for 72 hours and labeled 8C.

Example 9: Tasting of Sweetener Compositions Comprising Chitosan

Each tester is given 4 mg of sucrose and 8A solid and 6 mg from each syrups 8B and 8C. The results are shown in Table 9.

TABLE 9

| Taster | Sucrose | 8A | 8B | 8C |
|---|---|---|---|---|
| Taster 1 | X | X+ After taste | X+ Slightly sweeter | X+ Barely, not as impressive as the powder samples |
| Taster 2 | X | More than X+ | X+ | X+ |
| Taster 3 | X | X+ After taste | X+ Residual | X |
| Taster 4 | X | X After taste | X | X+ more than previous |
| Taster 5 | X | X+ After taste | X+ Very slightly, after taste | X+ |

Key: X represents a level of sweetness, X+ represents a taste that is more sweet than X Example 10: Sweetener Compositions Comprising Glucose Monohydrate The following general procedure is used to make each composition 10A-10F: Glucose monohydrate (15 g, pure, food-grade) is transferred into a mechanical grinder, 1.10 gr (8%) of carrier compound is added, and the mixture is ground for 20 sec. After a sample is taken, the mixture is transferred into a mortar and pestle for another 10 min of grinding. A sample is taken from the ground mixture. The remaining ground mixture is sonicated for 30 min at 40° C. and then passed through a sieve (70 mesh).

This experiment is repeated for each sample 10A-10E, selecting the carrier compound to produce compositions as follows:

10A—Glucose monohydrate (no carrier compounds used)—ground and sieved

10B—8% Perkasil® in glucose monohydrate

10C—8% CN001 (chitosan 200 nm particle size) in glucose monohydrate

10D—8% SCP-1 (chitosan 200 mesh particle size) in glucose monohydrate

Example 11: Taste Test of Sweetener Compositions Comprising Glucose Monohydrate Each taster is given 4 mg of each of the solid sweetener compositions. The results are described in Table 11 (with a repetition of 10C and 10D.).

TABLE 11

| Taster | Glucose monohydrate 10A | 10B | 10C | 10C | 10D | 10D |
|---|---|---|---|---|---|---|
| Taster 1 | X Barely any sweetness | X++ | X+ | X+ | X+ Very weak | X Weak |
| Taster 2 | X Barely any sweetness | X++ | X+ | X+ | X+ | X Weak |
| Taster 3 | X Barely any sweetness | X++ | X+ Slightly, spread | X+ Very slightly sweeter | X+ Very weak | X Weak |

Key: X represents a level of sweetness, X+ represents a taste that is more sweet than X, X++ represents a taste that is more sweet than X+

Example 12: Formation of Sweetener Compositions with Other Carrier Compounds 15 gr of sucrose are transferred into a mechanical grinder, 1.2 gr (8%) of carrier are added, and the mixture is ground for 20 sec. After a sample is taken, the mixture is transferred into a mortar and pestle for another 10 min of grinding. A sample is taken from the ground mixture. The remaining ground mixture is sonicated for 30 min at 40° C. Samples are sieved (70 mesh). Each taster is given 4 mg of the following samples and the results are shown in Table 12:

12A—Sucrose

12B—8% CN001 (Chitosan, particle size—200 nm) in sucrose

12C—8% FGC-2 (Chitosan, particle size—80 mesh) in sucrose

12D—8% Avicel® LM 310 (Maltodextrin) in sucrose

12E—8% Avicel® GP 1030 (Maltodextrin) in sucrose

TABLE 12

| Taster | Sucrose 12A | 12B (Chitosan 200 nm) | 12C (Chitosan, 80 mesh) | 12D (Maltodextrin - Avicel® LM 310) | 12E (Maltodextrin - Avicel® GP 1030) |
|---|---|---|---|---|---|
| Taster 1 | X | X++ | X+ | X+ A bit less than 143 | X+ A bit less than previous |
| Taster 2 | X | X++ | X+ | X+ A bit less than 143 | X+ Better texture |

Key: X represents a level of sweetness, X+ represents a taste that is more sweet than X, X++ represents a taste that is more sweet than X+

Example 13: Formation of Sweetener Compositions with Other Carrier Compounds 15 gr of sucrose are transferred into a mechanical grinder, 1.2 gr (8%) of carrier compound is added, and the mixture is ground for 20 sec. After a sample is taken, the mixture is transferred into a mortar and pestle for another 10 min of grinding. A sample is taken from the ground mixture. The remaining ground mixture is sonicated for 30 min at 40° C.

13A—Sucrose

13B—8% CN001 (Chitosan, particle size—200 nm) in sucrose

13C—8% CN002 (Chitosan, particle size—200 nm) in sucrose

13D—8% SCP-1 (Chitosan, particle size—200 mesh) in sucrose

13E—8% SCP-2 (Chitosan, particle size—200 mesh) in sucrose

13F—8% FGC-2 (Chitosan, particle size—80 mesh) in sucrose

13G—8% Avicel® LM 310 (Maltodextrin) in sucrose

13H—8% Avicel® GP 1030 (Maltodextrin) in sucrose

Samples are sieved. Each taster is given 4 mg of the following samples and the results are shown in

TABLE 13

| Taster | Sucrose 13A | 13B | 13C | 13D | 13E | 13F | 13G | 13H |
|---|---|---|---|---|---|---|---|---|
| Taster 1 | X | X++ | X++ | X++ | X+ | X+ | X+ | X+ small |
| Taster 2 | X | X+ | X++ | X++ | X+ | X++ | X+ | X+ small |
| Taster 3 | X | X++ | X++ | X++ | X+ | X++ Maybe more | X+ | X+ small |

Key: X represents a level of sweetness, X+ represents a taste that is more sweet than X, X++ represents a taste that is more sweet than X+

Example 14: Sensory Test Procedure

The tests are participated by a panel of 8 tasting experts who have been sensory tested in the past. All participants have been trained. The tests are divided into the following 4 segments:

a) Testing the tasters sensory threshold b) Calibration c) Sucrose versus S1 composition tastings—in powder and syrup form d) Sucrose versus S1 composition tastings—powders mixed in a separate medium Tasting process: All tasting stages excluding calibration, are conducted in the form of a "triangle test": each participant is given three samples marked with random numbers that include two identical samples and one dissimilar sample. Participants are instructed to name the different sample in each set and explain the difference in their opinion.

Participants are given two sets of tests in each tasting, where one test included a single reference sample and the other contained two.

Sensory threshold: Panel participants are given seven triangle tests that included various concentrations of sucrose dissolved in water.

Calibration step: This step is added to the tasting process as another form of tasting the panel's sensory threshold for sweetness. All panel members are given two samples of sucrose marked "A" and "B" the samples were of 4 mg and 5 mg respectively in the purpose of testing the panel's ability to recognize such delicate variations.

The rest of the tests were conducted similarly—each sample is tested with sucrose as reference in two sets of triangle tests.

Example 15: Amount of Perkasil® in Sweetener Compositions

Several compositions are prepared as described herein (Example 3) but the amount of Perkasil® is varied among samples and taste testers consume 4 mg of each sample to judge the taste and sweetness with respect to amount of Perkasil®. The results are displayed in Table 15 (each "+" indicates more sweetness).

TABLE 15

|  | Sucrose syrup | 6% Perkasil ® - mixed powders to sucrose syrup | 6% Perkasil ® - Perkasil added to sucrose syrup | 10% Perkasil ® - mixed powders to sucrose syrup | 10% Perkasil ® - Perkasil added to sucrose syrup |
|---|---|---|---|---|---|
| Tester 1 | X | X+ Small variation | X+ Small variation | X++ 1.5 times sweeter than sucrose Residual taste | X+ |
| Tester 2 | X | X+ Small variation | X+ | X+ | X |
| Tester 3 | X | X+ Small variation, Different texture | X+ Different texture | X++ 1.5 times sweeter than sucrose Residual taste | X+ |
| Tester 4 | X | X+ Small variation | X+ Small variation | X+ Small variation | X+ |

Key: X represents a level of sweetness, X+ represents a taste that is more sweet than X, X++ represents a taste that is more sweet than X+

It is noted that the 6% and 10% Perkasil® compounds are sweeter than the sucrose syrup composition that lacks Perkasil®. Additionally, the compositions with 6% and 10% Perkasil are less sweet than the corresponding 8% Perkasil® composition.

Example 16: Formation of Sweetener Compositions Comprising Sweetener Polyol

A) 1.0 gram of Maltitol and 0.08 gram Perkasil® are ground together as solids manually using a mortar and pestle for 10 min to form an maltitol sweetener composition with 8% silica wt/wt. The resulting powdered mixture is sonicated at 40° C. for 30 min, then sieved (70 mesh). The resulting sweetener composition, 16A, is stored in a refrigerator until tested.

B) Sorbitol (5.0 gram) and Perkasil® (0.4 gram) are ground together for 20 sec in a mechanical Moulinex grinder. The resulting mixture is transferred to a mortar and pestle and ground manually for 10 min. The resulting powdered mixture is sonicated at 40° C. for 30 min and then sieved to produce the final sweetener composition comprising sorbitol and Perkasil® (8% wt/wt), 16B.

C) Xylitol (5.0 gram) and Perkasil® (0.4 gram) are ground together for 20 sec in a mechanical Moulinex grinder. The resulting mixture is transferred to a mortar and pestle and ground manually for 10 min. The resulting powdered mixture is sonicated at 40° C. for 30 min and then sieved to produce the final sweetener composition comprising xylitol and Perkasil® (8% wt/wt), 16C.

Example 17: Taste Test of Sweetener Compositions Comprising Sweetener Polyols

Tasters each consume a sample of 5 mg of each of the following 6 sweetener compositions: maltitol, 16A, sorbitol, 16B, xylitol, and 16C, and record their observations after each test. The observations are recorded in the following table:

|  | Maltitol | 16A | Sorbitol | 16B | Xylitol | 16C |
|---|---|---|---|---|---|---|
| Tester 1 | After taste, barely sweet | X+ | Sweeter than Maltitol Y | Y | Sweetest polyol so far Z | Z++ |
| Tester 2 | Some sweetness X | X+ | Much sweeter than Maltitol Y | Y+ | Very sweet Zn | Z+ |
| Tester 3 | Some sweetness X | X++ | Less sweet than Maltitol Y | Y+ 0.5 | Sweeter than sucrose Z | Z+ 1.5 |
| Tester 4 | Less than sucrose X | X+ 0.5 | Similar to Glucose Y | Y+ fades | As sweet as Sorbitol, fades Z | Z+ |

-continued

|  | Maltitol | 16A | Sorbitol | 16B | Xylitol | 16C |
|---|---|---|---|---|---|---|
| Tester 5 | Less than sucrose X | X+ 0.5 | Fades Y | Y+ 0.5 | Very sweet fades quickly Z | Z+ 0.5 Sample spread |

Key: X represents a level of sweetness, X+ represents a taste that is more sweet than X, X++ represents a taste that is more sweet than X+.
Y represents a level of sweetness, Y+ represents a taste that is more sweet than Y, Y++ represents a taste that is more sweet than Y+.
Z represents a level of sweetness, Z+ represents a taste that is more sweet than Z, Z++ represents a taste that is more sweet than Z+.

Example 18: Formation of Sweetener Compositions Comprising High Intensity Sweeteners and Sucrose A) Aspartame (5 mg) and sucrose (1.0 gram) are ground together manually with a mortar and pestle for 10 min. The resulting mixture is sonicated at 40° C. for 30 min, and the powdered mixture is sieved to produce the product sweetener composition 18A.

B) Acesulfame potassium (Acesulfame K) (10 mg) and sucrose (2.0 gram) are ground together manually with a mortar and pestle for 10 min. The resulting mixture is sonicated at 40° C. for 30 min, and the powdered mixture is sieved to produce the product sweetener composition 18B.

C) A gram scale portion (e.g. about 1.0 gram) of saccharin is ground in a Moulinex mechanical grinder for to reduce the particle size. A small portion of the ground saccharin (10 mg) is combined with sucrose (2.0 gram), and the solids are ground together manually with a mortar and pestle for 10 min. The resulting mixture is sonicated at 40° C. for 30 min, and the powdered mixture is sieved to produce the product sweetener composition 18C.

D) Sodium cyclamate (10 mg) and sucrose (2.0 gram) are ground together manually with a mortar and pestle for 10 min. The resulting mixture is sonicated at 40° C. for 30 min, and the powdered mixture is sieved to produce the product sweetener composition 18D.

Example 19: Formation of Sweetener Compositions Comprising High Intensity Sweeteners, Sucrose, and Silica A) Aspartame (10 mg), sucrose (2.0 gram), and Perkasil® SM 660 (0.16 gr) are ground together manually with a mortar and pestle for 10 min. The resulting mixture is sonicated at 40° C. for 30 min, and the powdered mixture is sieved to produce the product sweetener composition 19A.

B) Acesulfame K (10 mg), sucrose (2.0 gram), and Perkasil® SM 660 (0.16 gr) are ground together manually with a mortar and pestle for 10 min. The resulting mixture is sonicated at 40° C. for 30 min, and the powdered mixture is sieved to produce the product sweetener composition 19B.

C) A gram scale portion of saccharin is ground in a Moulinex mechanical grinder to reduce the particle size. A small portion of the ground saccharin (10 mg) is combined with Perkasil® SM 660 (0.16 gr), and sucrose (2.0 gram), and the solids are ground together manually with a mortar and pestle for 10 min. The resulting mixture is sonicated at 40° C. for 30 min, and the powdered mixture is sieved to produce the product sweetener composition 19C.

D) Sodium cyclamate (10 mg), sucrose (2.0 gram), and Perkasil® SM 660 (0.16 gr) are ground together manually with a mortar and pestle for 10 min. The resulting mixture is sonicated at 40° C. for 30 min, and the powdered mixture is sieved to produce the product sweetener composition 19D.

Example 20: Taste Test of Sweetener Compositions Comprising High Intensity Sweeteners, Sucrose and Optionally Silica Each taster consumes a sample of each of the following 8 samples: 18A, 18B, 18C, 18D, 19A, 19B, 19C and 19D, and records their observations after each test. The amount of each sample given to each tester is normalized by the sweetness factor of the High Intensity Sweetener included according to the following table:

| Sweetener | RS (of pure sweetener) | Sweetness intensity (of sample) | Tasting sample weight [mg] |
|---|---|---|---|
| Aspartame | 200 | 2 | 2.5 |
| Acesulfame K | 200 | 2 | 2.5 |
| Saccharin | 300 | 2.5 | 2 |
| Sodium cyclamate | 40 | 1.2 | 4.2 |

Thus, each tester consumes 2.5 mg of samples comprising Aspartame (18A and 19A), 2.5 mg of samples comprising Acesulfame K (18B and 19B), 2.0 mg of samples comprising Saccharin (18C and 19C), and 4.2 mg of samples comprising Sodium cyclamate (18D and 19D).

The observations made by each tester are recorded in the following table:

|  | Aspartame | | Acesulfame K | | Saccharin | | Sodium cyclamate | |
|---|---|---|---|---|---|---|---|---|
|  | 18A | 19A | 18B | 19B | 18C | 19C | 18D | 19D |
| Taster 1 | Sweet, less than sucrose, no bitterness X | X++ | Sweet with a metallic after taste Y | Y+ Less after taste | Sweet with a metallic after taste, leaves a sense of dryness Z | Increased after taste | Sweet with a cardboard after taste A | A+ Sweeter with enhanced after taste |
| Taster 2 | Sweeter than sucrose, | X | Sweet (less than X) no | Y+ No after taste | Very sweet Z | Z++ | Sweet A | A+ |

-continued

| | Aspartame | | Acesulfame K | | Saccharin | | Sodium cyclamate | |
|---|---|---|---|---|---|---|---|---|
| | 18A | 19A | 18B | 19B | 18C | 19C | 18D | 19D |
| | different sweetness X | after taste Y | | | | | | |
| Taster 3 | Sweeter than sucrose, lingers X | X The same | After taste Y | Y+ After taste | Very sweet, a sense of dryness Z | Z Same as NG363 | Sweetest HIS so far No after taste A | Cardboard after taste |
| Taster 4 | Less than sucrose X | X After taste | Weak sweetness, after taste Y | Y+ Slightly less after taste | Very sweet, a sense of dryness Z | Z++ Very sweet, increased after taste | Very sweet (slightly more than NG363) A | A+ Sweet with a cardboard after taste |

Key: X represents a level of sweetness, X+ represents a taste that is more sweet than X, X++ represents a taste that is more sweet than X+.
Y represents a level of sweetness, Y+ represents a taste that is more sweet than Y, Y++ represents a taste that is more sweet than Y+.
Z represents a level of sweetness, Z+ represents a taste that is more sweet than Z, Z++ represents a taste that is more sweet than Z+.
A represents a level of sweetness, A+ represents a taste that is more sweet than A.

Example 21: Formation of Sweetener Compositions Comprising High Fructose Corn Syrup A) Perkasil® SM 660 (1.5 gram), is added in portions to 26.8 gram High Fructose Corn Syrup Isoglucose F42 (70% total sugar by weight; 42% fructose/58% glucose, dry solid wt/wt) while stirring to produce a ratio of 8% silica to total sugar content (wt/wt). The clear yellow dispersion is sonicated for 30 min at 40° C. The mixture is cooled to room temperature to produce the final sweetener composition, 21A.

B) Perkasil® SM 660 (0.9 gram), is added in portions to 27.0 gram High Fructose Corn Syrup Isoglucose F42 (70% total sugar by weight; 42% fructose/58% glucose, dry solid wt/wt) while stirring to produce a ratio of 8% silica to glucose content (wt/wt). The clear yellow dispersion is sonicated for 30 min at 40° C. The mixture is cooled to room temperature to produce the final sweetener composition, 21B.

C) Perkasil® SM 660 (1.5 gram), is added in portions to 26.1 gram High Fructose Corn Syrup Isoglucose F50 (72% total sugar by weight; 50% fructose, 47% glucose dry solid, wt/wt) while stirring to produce a ratio of 8% silica to total sugar content (wt/wt). The clear yellow dispersion is sonicated for 30 min at 40° C. The mixture is cooled to room temperature to produce the final sweetener composition, 21C.

D) Perkasil® SM 660 (0.7 gram), is added in portions to 26.0 gram High Fructose Corn Syrup Isoglucose F50 (72% total sugar by weight; 50% fructose, 47% glucose dry solid, wt/wt) while stirring to produce a ratio of 8% silica to glucose content (wt/wt). The clear yellow dispersion is sonicated for 30 min at 40° C. The mixture is cooled to room temperature to produce the final sweetener composition, 21D.

Example 22: Taste Test of Sweetener Compositions Comprising High Fructose Corn Syrup Each taster is given each sample twice (7 mg) of each of the following 6 sweetener compositions sequentially: Isoglucose F42 (Galam), 21A, 21B, Isoglucose F50 (Galam), 21C, 21D, and records their observations after each test. The observations are recorded in the following table:

| | Isoglucose F42 | 21A | 21B | Isoglucose F50 | 21C | 21D |
|---|---|---|---|---|---|---|
| Taster 1 | X | X+ 1 | X+ 2 | Y | Y+ 1 | Y+ 1 |
| Taster 2 | X | X+ 1.5 | X+ | Y Sweeter than F42 | Y+ 1 | Y+ 1 |
| Taster 3 | X | X+ 1 | X | Y Sweeter than F42 | Y | Y+ 0.5 |
| Taster 4 | X | X+ 1.5 | X+ 1.5 | Y | Y | Y+ 1.5 |
| Taster 5 | X | X+ 1 | X+ 1 | Y | Y+ 1 | Y+ 1 |

Key: X represents a level of sweetness, X+ 0.5 represents a taste that is sweeter than X, X+ 1 represents a taste that is sweeter than X+ 0.5, X+ 1.5 represents a taste that is sweeter than X+ 1, X+ 2 represents a taste that is more sweet than X+ 1.5.
Y represents a level of sweetness, Y+ 0.5 represents a taste that is more sweet than Y, Y+ 1 represents a taste that is more sweet than Y+ 0.5, Y+ 1.5 represents a taste that is more sweet than Y+ 1.

Example 23: Formation of Hard Candy Comprising Enhanced Sweetener Compositions 154.023 g of High Fructose Corn Syrup (HFCS) Isoglucose F42 is added to 98 g of sucrose and mixed in a pot over medium heat until the sucrose completely dissolves. 60 g of water is added, and the solution is stirred with a whisk. The liquid is heated to a temperature of 149° C. Immediately afterwards it is poured into a mold and cooled at room temperature to produce the final hard candy, 23A.

92.406 g of HFCS+S1 (Isoglucose F42 with 8% Perkasil to glucose content (wt/wt)) is added to 60 g of water and mixed in a pot over medium heat. 98 g of sucrose is added, and the solution is stirred with a whisk. The liquid is heated to a temperature of 149° C. Immediately afterwards it is poured into a mold and cooled at room temperature to produce the final hard candy, 23B.

154.015 g of HFCS Isoglucose F42 is added to 60 g of water and mixed in a pot over medium heat. 58.80 g of the S1 composition is added, and the solution is stirred with a whisk. The liquid is heated to a temperature of 149° C. Afterwards it is poured into a mold and cooled at room temperature to produce the final hard candy, 23C.

Example 24: Taste Test of Hard Candy Comprising Enhanced Sweetener Compositions

Each taster is given each of the following 4 hard candies and records their observations after each test. The observations are recorded in the following table:

| Taster | 23A | 23B | 23C |
|---|---|---|---|
| Taster 1 | X | X + 1 | X + 2 |
| Taster 2 | X | X + 1<br>Different sweetness,<br>longer sweet taste. | X + 1<br>Caramel notes |
| Taster 3 | X | X + 1<br>Late sweetness. | X + 2 |

Example 25: Formation of Meringue Comprising Enhanced Sweetener Compositions Oven is preheated to 93.3° C. (200° F.). A pinch of the S1 composition is added to the egg whites (97 g) before whipping. The egg whites are whipped on a low setting in a stainless steel or ceramic bowl. The remaining S1 composition (82.5 g for 50% sugar reduction, 99 g for 40% sugar reduction) is divided into five equal portions. After about a minute of whipping, the egg whites become foamy and one portion of the S1 composition is added slowly to the egg whites. After about 1.5-2 minutes, the egg whites expand in volume by two to three-fold and another portion of the S1 composition is added slowly. In 1.5 minute increments, the remaining portions of S1 composition are added slowly. The meringue is whipped until a stiff peak consistency is reached. The meringue is then transferred to a piping bag and is piped into a non-stick pan that can be lined with silicone or parchment paper. The meringue is baked for 3 hours, with the pan rotated every hour. For the control meringue, 165 g of sucrose is used in place of the S1 composition.

Example 26: Taste Test of Meringue Comprising Enhanced Sweetener Compositions 5 trained and experienced panelists assess the meringue samples from Example 25 in a round table discussion tasting format. The sugar Control is assessed and a reference score (using the 0-100 intensity scale) for Overall Sweetness is discussed and agreed to. Sugar Reduction samples containing S1 composition are then tasted and consensus scores are agreed upon for overall sweetness. Notes are also made on other appearance, aroma, flavor, texture, and aftertaste attributes of each sample. Individual overall sweetness intensity ratings for all samples (coded) are then carried out in sensory booths, in duplicate, using the 0-100 line scale. Analysis of data is carried out to establish if there are any differences between the sugar control and each of the Sugar Reduction formulations for Overall Sweetness.

Tasting of Control: Not very much immediate sweetness but then grew. Overall sweetness agreed as about 55 on 0-100 point scale. Some additional slight flavors of malt and egg white. Moderately high initial bite and fast rate of breakdown in texture. Sweetness and some bitterness in aftertaste.

Tasting of 50% Sugar Reduction Sample: Sweetness close to Control. Some barley sugar flavor and chalky flavor. Some chalkiness in texture.

Tasting of 40% Sugar Reduction Sample: Sweeter than control. Slight chalkiness but much less than 50% Sugar Reduction Sample.

Overall sweetness rating scores on a 0-100 intensity scale for 5 panelists in duplicate tastings are shown.

| Sample | Overall Sweetness |
|---|---|
| Control | 52.2 |
| 50% Sugar Reduction | 53.9 |
| 40% Sugar Reduction | 70.5 |

Example 27: Formation of Whipped Cream Comprising Enhanced Sweetener Compositions Double cream (223 g, Sainsbury) is used for preparing the samples. The S1 composition (13.83 g for 35% sugar reduction, 14.9 g for 30% sugar reduction) is added gradually after two minutes of whipping the cream, while the hand mixer (low setting) whipped the cream to the desired consistency. For the control whipped cream, sucrose (21.28 g) is used in place of the S1 composition. For the Stevia whipped cream, Stevia extract (0.1059 g) is used in place of the S1 composition.

Example 28: Taste Test of Whipped Cream Comprising Enhanced Sweetener Compositions Control, 35% Sugar Reduction, 30% Sugar Reduction, and Stevia whipped cream samples are evaluated using Descriptive Sensory Profiling with a panel of eleven trained assessors. Two 2 hr discussion and training sessions are held. During these sessions, the panel evaluates all products and developed and agrees to a descriptive vocabulary covering appearance, aroma, flavor, texture, mouthfeel, and aftertaste characteristics of the samples. Assessors carry out formal attribute intensity rating of all samples, working alone in individual sensory evaluation booths. Ratings are made using a 100 point unstructured line scale, with verbal anchors, from low to high. Each sample is presented to the assessors labeled with a three digit code and is evaluated three times by each assessor during a 2.5 hr session. Samples are presented according to a balanced design. Evaluations are made in mouth, immediately after swallowing, one minute after swallowing, and two minutes after swallowing for key residual after effects. Plain crackers and mineral water are used as palate cleansers between samples. All samples are assessed in tasting booths designed to ISO 8589:2007, illuminated with Northern daylight. As part of the training, the panel agrees to a reference score of 80 for the overall sweetness of the whipped double cream control sample. The reduced sugar samples containing the S1 composition are then compared to the control. The sample order is randomized to avoid potential bias. Data for each attribute is analyzed using analysis of variance to identify attributes that discriminate samples at the 5% level of significance ($P<0.05$).

Whipped Double Cream: Appearance and Aroma

| Attributes | 35% Sugar Reduction | | 30% Sugar Reduction | | Control | | Stevia | |
|---|---|---|---|---|---|---|---|---|
| Number of Surface Holes Appearance | 21.1 | a | 21.4 | a | 22.8 | a | 22.3 | a |
| Size of Surface Holes Appearance | 17.6 | a | 17.6 | a | 21.6 | a | 16.7 | a |
| Depth of Color Appearance* | 65.1 | a | 61.7 | ab | 59.6 | b | 59.8 | b |
| Whipped Appearance | 63.7 | a | 64.2 | a | 64.5 | a | 60.3 | a |
| Overall Aroma | 22.6 | a | 20.5 | a | 24.4 | a | 21.9 | a |

-continued

| Attributes | 35% Sugar Reduction | | 30% Sugar Reduction | | Control | | Stevia | |
|---|---|---|---|---|---|---|---|---|
| Creamy Aroma* | 23.0 | ab | 18.8 | b | 25.6 | a | 19.4 | ab |
| Cooked Sugar Aroma | 3.0 | a | 3.9 | a | 4.2 | a | 1.6 | a |

*Indicates a significant difference at the 95% confidence level.
Where samples share the same letter, there is no significant difference at the 95% confidence level All samples are very similar in appearance. Only the 35% Sugar Reduction sample is significantly creamier in color compared to the Control and Stevia samples. All samples have a similar creamy aroma. Only the 35% Sugar Reduction sample is significantly lower compared to the Control. All other samples are comparable.

Whipped Double Cream: Flavor in Mouth

| Attributes | 35% Sugar Reduction | | 30% Sugar Reduction | | Control | | Stevia | |
|---|---|---|---|---|---|---|---|---|
| Sweetness Onset Flavor* | 10.8 | b | 12.9 | ab | 10.5 | b | 15.7 | a |
| Sweetness Build Flavor* | 28.0 | b | 30.7 | b | 31.3 | b | 46.8 | a |
| Overall Sweetness Flavor | 57.4 | a | 58.5 | a | 65.5 | a | 60.4 | a |
| Bitter Flavor* | 2.1 | b | 3.3 | b | 0.2 | b | 30.8 | a |
| Creamy Flavor* | 51.6 | a | 50.7 | a | 53.9 | a | 40.8 | b |
| Liquorice Flavor* | 0.2 | b | 0.1 | b | 0.3 | b | 67.5 | a |
| Metallic Flavor* | 1.6 | b | 4.8 | b | 0.7 | b | 23.3 | a |

*Indicates a significant difference at the 95% confidence level.
Where samples share the same letter, there is no significant difference at the 95% confidence level Both Sugar Reduction samples are deemed to be equivalently sweet to the Control and Stevia samples while in the mouth. Sugar reduction samples are also at parity with the Control for Sweetness Onset and Build. There are no significant differences in any other flavor attributes between the Sugar Reduction samples and the Control. However, the Stevia sample imparts far more detrimental flavors, the Sweetness takes longer to build compared to all other samples, and the sample is less Creamy and far more Bitter and Metallic tasting. The Stevia sample also has a strong Liquorice flavor, which is absent in all other samples.

Whipped Double Cream: Texture and Mouthfeel in Mouth

| Attributes | 35% Sugar Reduction | | 30% Sugar Reduction | | Control | | Stevia | |
|---|---|---|---|---|---|---|---|---|
| Smooth Texture | 70.3 | a | 71.2 | a | 73.4 | a | 73.4 | a |
| Soft Texture | 73.5 | a | 74.6 | a | 74.8 | a | 75.0 | a |
| Density Texture | 51.4 | a | 52.7 | a | 49.5 | a | 51.1 | a |
| Rate of Melt Texture* | 26.7 | b | 30.2 | ab | 26.3 | b | 32.1 | a |
| Oily Mouth Coating Mouthfeel | 25.7 | a | 29.2 | a | 24.8 | a | 28.7 | a |
| Salivating Mouthfeel* | 37.2 | b | 34.2 | b | 39.9 | ab | 45.0 | a |
| Mouth Drying Mouthfeel | 27.8 | a | 31.4 | a | 27.3 | a | 34.8 | a |

*Indicates a significant difference at the 95% confidence level.
Where samples share the same letter, there is no significant difference at the 95% confidence level There are no significant textural or mouthfeel differences between the Sugar Reduction and Control samples. The Stevia sample melts more quickly and is more Salivating compared to the 35% Sugar Reduction and Control samples. All samples are very soft and smooth with a middling firm density. A low oily mouth coating could be felt while the samples are broken down in the mouth, and all are comparably mouth drying at a low to moderate level.

Whipped Double Cream: Immediate Aftertaste

| Attributes | 35% Sugar Reduction | | 30% Sugar Reduction | | Control | | Stevia | |
|---|---|---|---|---|---|---|---|---|
| Overall Sweetness Aftertaste* | 46.9 | b | 50.7 | ab | 56.5 | a | 52.3 | ab |
| Bitter Aftertaste* | 4.5 | b | 4.3 | b | 2.1 | b | 34.9 | a |
| Creamy Aftertaste* | 44.8 | a | 46.1 | a | 47.0 | a | 36.0 | b |
| Liquorice Aftertaste* | 0.2 | b | 0.2 | b | 0.1 | b | 59.2 | a |
| Metallic Aftertaste* | 5.2 | b | 6.7 | b | 5.6 | b | 27.5 | b |
| Oily Mouth Coating Aftereffect | 25.8 | a | 27.5 | a | 24.3 | a | 23.9 | a |
| Salivating Aftereffect | 38.7 | a | 38.5 | a | 41.2 | a | 41.9 | a |
| Mouth Drying Aftereffect* | 38.1 | b | 40.4 | b | 38.6 | b | 49.1 | a |

*Indicates a significant difference at the 95% confidence level.
Where samples share the same letter, there is no significant difference at the 95% confidence level The 30% Sugar Reduction sample is at parity with the Control and Stevia samples for Overall Sweetness in Immediate Aftertaste. The 35% Sugar Reduction sample is significantly less sweet compared to Control at this stage, however by 1 minute it is equivalently sweet compared to the Control once again. The Stevia sample remains significantly more Bitter, Metallic, and Liquoricy tasting compared to the other samples. All samples leave a similarly low oily coating in the mouth and are moderately salivating. The Stevia sample is significantly more Mouth Drying compared to the rest of the samples.

Whipped Double Cream: Aftertaste at 1 Minute

| Attributes | 35% Sugar Reduction | | 30% Sugar Reduction | | Control | | Stevia | |
|---|---|---|---|---|---|---|---|---|
| Overall Sweetness Aftertaste | 41.0 | a | 41.1 | a | 47.5 | a | 45.9 | a |
| Bitter Aftertaste* | 6.1 | b | 3.7 | b | 3.9 | b | 31.5 | a |
| Creamy Aftertaste* | 38.3 | a | 37.3 | ab | 38.1 | a | 29.5 | b |
| Liquorice Aftertaste* | 0.1 | b | 0.2 | b | 0.2 | b | 51.6 | a |
| Metallic Aftertaste* | 8.0 | b | 7.7 | b | 5.2 | b | 29.0 | a |
| Oily Mouth Coating Aftereffect | 21.9 | a | 25.3 | a | 21.7 | a | 22.7 | a |
| Salivating Aftereffect* | 31.3 | ab | 29.6 | b | 36.3 | ab | 37.6 | a |
| Mouth Drying Aftereffect* | 47.3 | ab | 48.1 | ab | 42.5 | b | 51.5 | a |

*Indicates a significant difference at the 95% confidence level.
Where samples share the same letter, there is no significant difference at the 95% confidence level 1 Minute after Swallowing all samples are equivalently sweet overall. The Stevia sample remains significantly more Bitter, Metallic, and Liquorice tasting compared to the other samples. All samples leave a similarly low oily coating in the mouth and are moderately salivating. The Stevia sample is significantly more Mouth Drying compared to the rest of the samples.

Whipped Double Cream: Aftertaste at 2 Minutes

| Attributes | 35% Sugar Reduction | | 30% Sugar Reduction | | Control | | Stevia | |
|---|---|---|---|---|---|---|---|---|
| Liquorice Aftertaste* | 0.4 | b | 0.2 | b | 0.2 | b | 47.1 | a |
| Tingling Aftereffect | 11.0 | a | 13.6 | a | 10.3 | a | 14.8 | a |
| Numbing Aftereffect | 18.6 | a | 22.0 | a | 20.3 | a | 19.7 | a |
| Mouth Drying Aftereffect | 48.4 | a | 49.0 | a | 46.5 | a | 51.0 | a |

*Indicates a significant difference at the 95% confidence level.
Where samples share the same letter, there is no significant difference at the 95% confidence level Even 2 minutes after swallowing, the Stevia sample continues to impart significantly stronger Liquorice flavors at a moderate intensity. By 2 minutes, all samples are at parity for after effects; both Numbering and Tingling are felt at low levels. Mouth Drying persists in all samples at a comparably moderate level.

Overall Sweet Flavor intensity as a function of time for whipped double cream samples is shown in FIG. 1. Although the control is numerically slightly sweeter at all time points, the differences for the most part are very small and are not statistically significant. All samples starts off moderately high in Sweet intensity. Although there is a drop in sweet flavor in all, samples retain a moderate sweet aftertaste by 1 minute. Immediately after swallowing the 35% Sugar Reduction sample is significantly less sweet compared to the Control; by 1 minute it is at parity with the Control once more. There is no significant difference in Overall Sweetness between the 35% and 30% Sugar Reduction samples containing the S1 composition.

Figure 2:
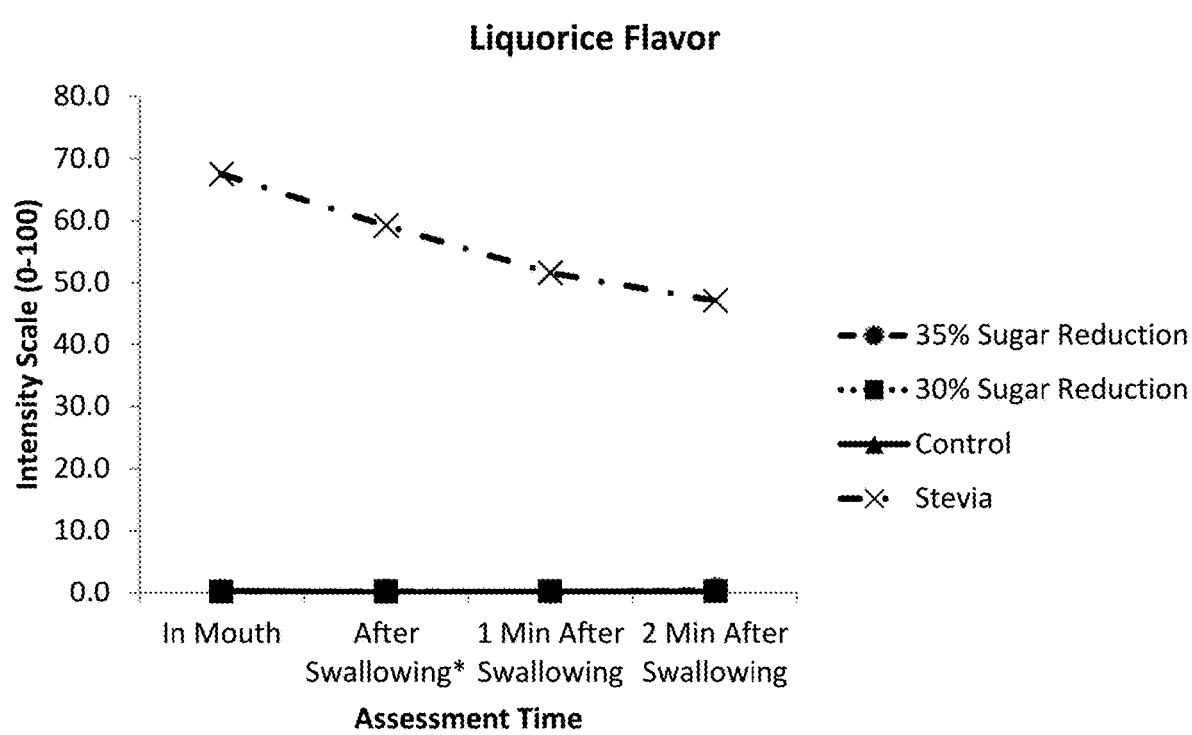
FIG. 2 shows liquorice flavor intensity as a function of time for whipped double cream samples.

Liquorice Flavor intensity as a function of time for whipped double cream samples is shown in FIG. 2. The Liquorice flavor is a unique and detrimentally perceived characteristic of the Stevia sample that makes it stand out from the rest of the samples being profiled. The flavor is significantly stronger in the Stevia sample for the duration of the rating. The flavor starts off strong in the mouth and reduces over time leaving a moderately intense aftertaste by 2 minutes.

Figure 3:
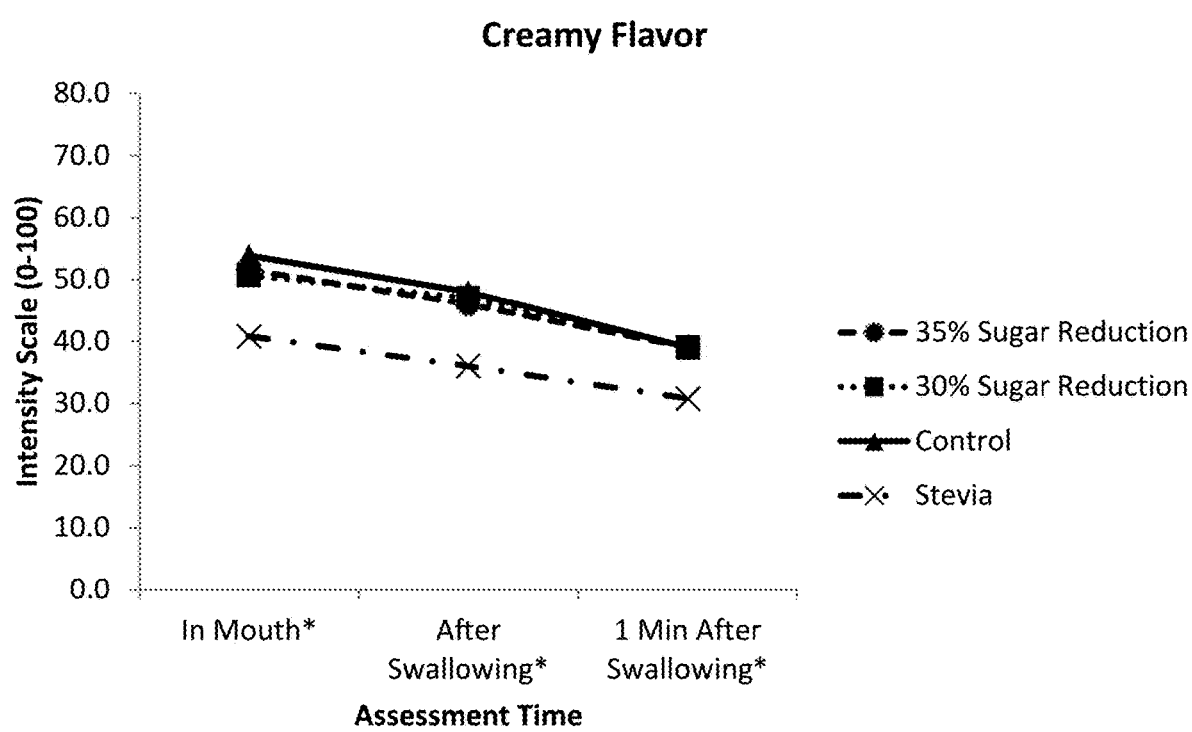
FIG. 3 shows creamy flavor intensity as a function of time for whipped double cream samples.

Creamy Flavor intensity as a function of time for whipped double cream samples is shown in FIG. 3. The Reduced Sugar samples and Control are comparably creamy at all time points. All three are significantly higher compared to the Stevia sample.

Figure 4:
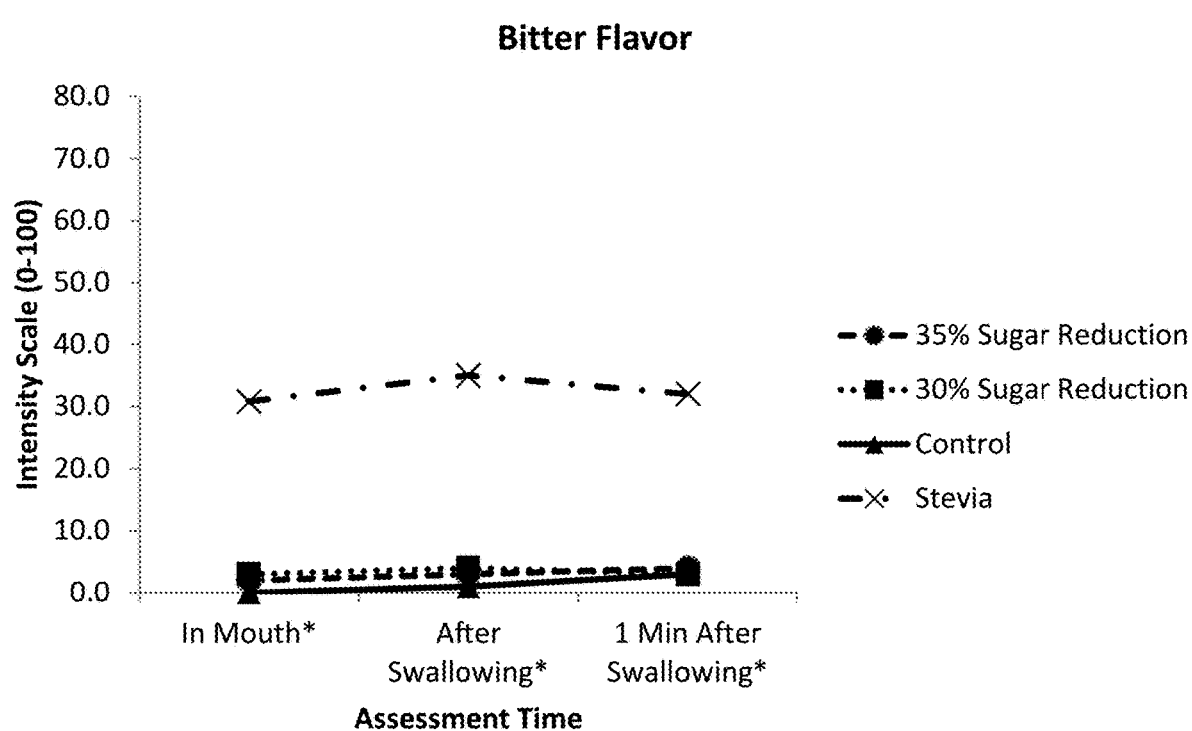
FIG. 4 shows bitter flavor intensity as a function of time for whipped double cream samples.

Bitter Flavor intensity as a function of time for whipped double cream samples is shown in FIG. 4. Bitterness is not a key flavor feature in the Control or Sugar Reduced samples containing the S1 composition. Bitterness remains significantly higher, at a low-moderate intensity, in the Stevia sample compared to the rest of the sample set.

Figure 5:
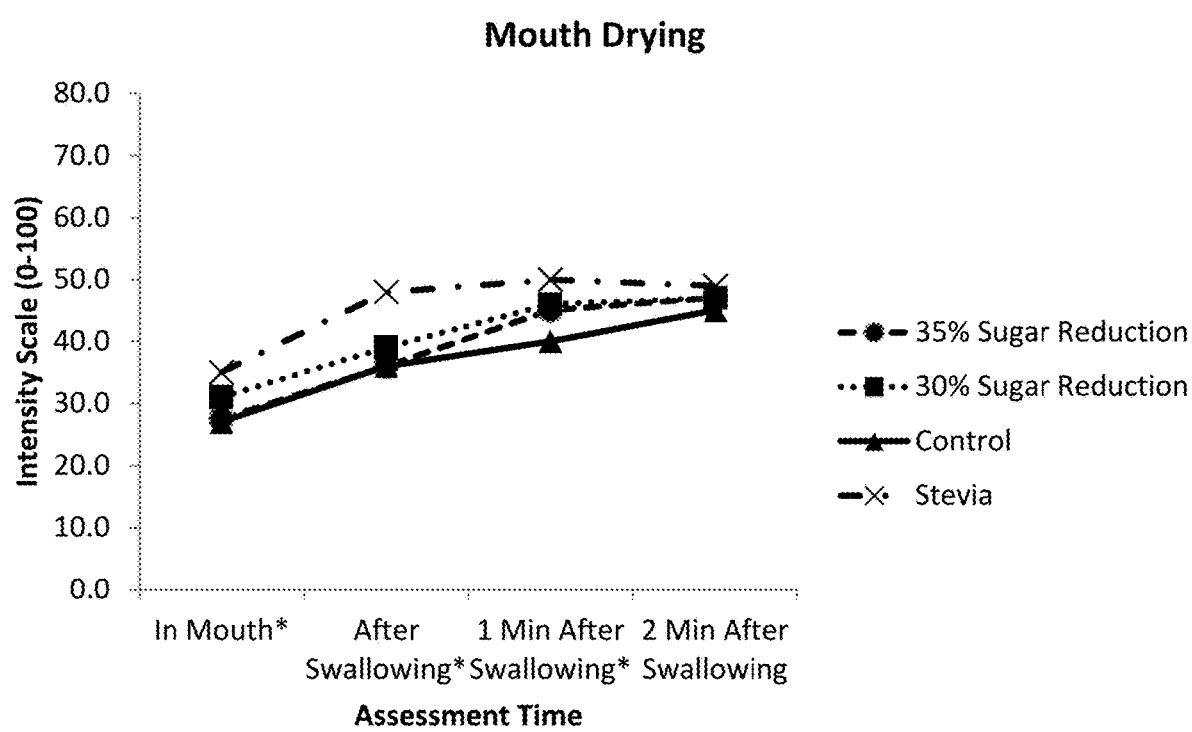
FIG. 5 shows mouth drying intensity as a function of time for whipped double cream samples.

Mouth Drying intensity as a function of time for whipped double cream samples is shown in FIG. 5. Mouth Drying is perceived at a similarly low level in all samples while the whipped double cream is in mouth. Mouth Drying increases for all samples once swallowed, significantly more so in the Stevia sample compared to the other samples. Drying continues to increase by 1 minute, however the Stevia sample is only significantly more drying compared to the Control. The 35% and 30% Reduced Sugar samples are at parity with both the Stevia sample and the Control, and by 2 minutes all samples peak, leaving similarly moderate levels of Mouth Drying.

Overall the Sugar Reduction samples containing the S1 composition offer a very similar sensory profile compared to the Control for all modalities. Both Sugar Reductions containing the S1 composition are equivalently sweet compared to the Control and Stevia sample while in the mouth and 1 minute after swallowing. The 35% Sugar Reduction sample is significantly less sweet compared to the Control immediately after the cream is swallowed. The 35% and 30% Sugar Reduction whipped creams are no more mouth drying than the Control. The Stevia sample stands out due to its unique, intense, and residual liquorice flavor and its detrimental metallic and bitter flavors which are significantly stronger compared to the other samples. These notes clearly mask the creamy flavor, which is significantly lower compared to the other samples.

The present invention may be embodied in other specific forms without departing from the spirit or essential attributes thereof.

What is claimed is:

1. A sweetener composition comprising one or more sweetener carbohydrates and/or sweetener polyols and a carrier compound; wherein:
   a. the carrier compound is silica;
   b. the sweetener composition comprises from 0.01% to 4% carrier compound weight/weight relative to a sum total sweetener carbohydrate and sweetener polyol; and
   c. the sweetener composition has enhanced sweetness compared to a control composition; wherein the control composition consists of the same contents by identity and quantity as the sweetener composition but without the carrier compound.

2. The sweetener composition of claim 1, wherein the one or more sweetener carbohydrates are sucrose, glucose, maltose, lactose, high fructose corn syrup, high maltose corn syrup, or a combination thereof.

3. The sweetener composition of claim 2, wherein the one or more sweetener carbohydrates are sucrose, glucose, or a combination thereof.

4. The sweetener composition of claim 2, wherein the one or more sweetener carbohydrates are high fructose corn syrup.

5. The sweetener composition of claim 1, wherein the sweetener polyol is selected from the group consisting of xylitol, maltitol, erythritol, sorbitol, threitol, arabitol, hydrogenated starch hydrolysates (HSH), isomalt, lactitol, mannitol, galactitol (dulcitol), and a combination thereof.

6. The sweetener composition of claim 1, further comprising an artificial sweetener, a natural sugar substitute, or a combination thereof.

7. The sweetener composition of claim 1, wherein the sweetener composition is formulated as particles.

8. The sweetener composition of claim 7, wherein at least 50 percent of the particles are between about 25 microns and 200 microns in diameter, or wherein at least 50 percent of the particles are between 25 microns and 74 microns in diameter.

9. The sweetener composition of claim 1, wherein the carrier compound is precipitated silica, porous silica, silica gel, amorphous silica, or a combination thereof.

10. The sweetener composition of claim 1, wherein the composition comprises at least 90% sweetener carbohydrate or sweetener polyol and carrier compound by weight.

11. The sweetener composition of claim 1, wherein the composition consists essentially of water and the sweetener carbohydrate and/or sweetener polyol and carrier compound.

12. The sweetener composition of claim 1, wherein the carrier compound has an average particle size of up to 60 microns.

13. The sweetener composition of claim 1, wherein the carrier compound has a specific surface area of at least 120 m2/g.

14. The sweetener composition of claim 1, wherein the composition does not comprise DNA, protein, lignin, or magnetic particles.

15. A sweetener composition formulation comprising the sweetener composition of claim 1, wherein the formulation is a syrup.

16. A consumable composition comprising the sweetener composition of claim 1, wherein the consumable product is selected from the group consisting of food products, beverage products and pharmaceutical products.

17. The consumable composition of claim 16, wherein the consumable composition is less bitter than the control composition.

18. The consumable composition of claim 16, wherein the consumable composition comprises up to 2% silica w/w.

19. The sweetener composition of claim 1, wherein the sweetener composition comprises 0.01% to 2% silica.

20. The sweetener composition of claim 1, wherein the sweetener composition has lower caloric content as compared to the control composition.

\* \* \* \* \*